(12) United States Patent
Gephart

(10) Patent No.: US 11,344,346 B2
(45) Date of Patent: May 31, 2022

(54) BONE PLATE SYSTEM

(71) Applicant: Pioneer Surgical Technology, Inc., Marquette, MI (US)

(72) Inventor: Matthew P. Gephart, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 192 days.

(21) Appl. No.: 16/454,949

(22) Filed: Jun. 27, 2019

(65) Prior Publication Data

US 2020/0000501 A1    Jan. 2, 2020

Related U.S. Application Data

(60) Provisional application No. 62/692,464, filed on Jun. 29, 2018.

(51) Int. Cl.
*A61B 17/80*    (2006.01)
*A61B 17/86*    (2006.01)
(Continued)

(52) U.S. Cl.
CPC .......... *A61B 17/8047* (2013.01); *A61B 17/86* (2013.01); *A61B 2017/00862* (2013.01); *A61B 2017/564* (2013.01)

(58) Field of Classification Search
CPC ................................................ A61B 17/8047
See application file for complete search history.

(56) References Cited

U.S. PATENT DOCUMENTS

| 2,580,821 A | 1/1952 | Nicola |
| 3,710,789 A | 1/1973 | Ersek |

(Continued)

FOREIGN PATENT DOCUMENTS

| DE | 3808937 | 10/1989 |
| WO | 0062693 | 10/2000 |
| WO | 2012162733 | 12/2012 |

OTHER PUBLICATIONS

European Communication pursuant to Rules 161(2) and 162 EPC dated Feb. 9, 2021, in correspondng European Application No. 19824755.3 (3 pages).

(Continued)

*Primary Examiner* — Zade Coley
(74) *Attorney, Agent, or Firm* — Fitch, Even, Tabin & Flannery LLP

(57) ABSTRACT

In one aspect, a bone plate system that includes a bone plate having a plurality of elongated through openings. The bone plate system includes a plurality of bone screws and a plurality of sliders in the elongated through openings of the bone plate that receive the bone screws. The bone plate system includes at least one resilient member for being configured to apply a biasing force to each of the sliders to urge the slider toward one end portion of a respective through opening. Further, the bone plate system includes at least one actuator having an interference position in which the actuator inhibits shifting of the sliders toward the one end portion of the through opening and a clearance position in which the actuator permits the at least one resilient member to urge the sliders and the bone screws received therein toward the one end portion of the through openings.

28 Claims, 40 Drawing Sheets

(51) Int. Cl.
*A61B 17/56* (2006.01)
*A61B 17/00* (2006.01)

(56) References Cited

U.S. PATENT DOCUMENTS

| | | | |
|---|---|---|---|
| 3,900,025 | A | 8/1975 | Barnes, Jr. |
| 3,939,828 | A | 2/1976 | Mohr et al. |
| 4,364,382 | A | 12/1982 | Mennen |
| 5,026,390 | A | 6/1991 | Brown |
| 5,281,226 | A | 1/1994 | Davydov et al. |
| 5,423,816 | A | 6/1995 | Lin |
| 5,458,642 | A | 10/1995 | Beer et al. |
| 5,620,443 | A | 4/1997 | Gertzbein et al. |
| 5,713,900 | A | 2/1998 | Benzel et al. |
| 5,735,853 | A | 4/1998 | Olerud |
| 5,766,218 | A | 6/1998 | Arnott |
| 5,785,713 | A | 7/1998 | Jobe |
| 6,117,135 | A | 9/2000 | Schlaepfer |
| 6,136,002 | A | 10/2000 | Shih et al. |
| 6,342,055 | B1 | 1/2002 | Eisermann et al. |
| 6,645,207 | B2 | 11/2003 | Dixon et al. |
| 6,695,846 | B2 * | 2/2004 | Richelsoph ........ A61B 17/7059 606/290 |
| 6,719,793 | B2 | 4/2004 | McGee |
| 6,783,531 | B2 | 8/2004 | Allen |
| 6,986,771 | B2 | 1/2006 | Paul et al. |
| 7,008,427 | B2 | 3/2006 | Sevrain |
| 7,591,840 | B2 | 9/2009 | Suddaby |
| 7,749,256 | B2 | 7/2010 | Farris et al. |
| 7,763,056 | B2 | 7/2010 | Dalton |
| 7,833,256 | B2 | 11/2010 | Biedermann et al. |
| 7,857,836 | B2 | 12/2010 | Huebner et al. |
| 7,914,561 | B2 | 3/2011 | Konieczynski et al. |
| 7,931,679 | B2 | 4/2011 | Heggeness |
| 7,972,366 | B2 | 7/2011 | Richelsoph et al. |
| 7,993,380 | B2 | 8/2011 | Hawkes |
| 8,043,346 | B2 | 10/2011 | Markworth |
| 8,216,285 | B2 | 7/2012 | Markworth |
| 8,226,693 | B2 | 7/2012 | Reimels et al. |
| 8,257,404 | B2 | 9/2012 | Hack |
| 8,262,711 | B2 | 9/2012 | Hess |
| 8,500,737 | B2 | 8/2013 | Richelsoph et al. |
| 8,574,270 | B2 | 11/2013 | Hess et al. |
| 8,585,742 | B2 | 11/2013 | Windolf |
| 8,623,019 | B2 * | 1/2014 | Perrow ............... A61B 17/808 606/70 |
| 8,728,127 | B2 | 5/2014 | Stewart |
| 8,747,441 | B2 | 6/2014 | Konieczynski et al. |
| 8,758,347 | B2 | 6/2014 | Weiner et al. |
| 8,790,379 | B2 | 7/2014 | Bottlang et al. |
| 8,814,915 | B2 | 8/2014 | Hess et al. |
| 8,882,812 | B2 | 11/2014 | Hess et al. |
| 8,882,815 | B2 | 11/2014 | Bottlang et al. |
| 8,974,504 | B2 | 3/2015 | Hess et al. |
| 8,992,583 | B2 | 3/2015 | Bottlang et al. |
| 9,005,255 | B2 | 4/2015 | Lewis et al. |
| 9,005,257 | B2 | 4/2015 | Sun |
| 9,033,988 | B2 | 5/2015 | Gephart et al. |
| 9,095,388 | B2 | 8/2015 | Hess et al. |
| 9,198,769 | B2 | 12/2015 | Perrow et al. |
| 9,295,503 | B2 | 3/2016 | Frigg et al. |
| 9,295,508 | B2 | 3/2016 | Bottlang et al. |
| 9,351,774 | B2 | 5/2016 | Konieczynski et al. |
| 9,381,046 | B2 * | 7/2016 | Perrow ............... A61B 17/808 |
| 9,408,647 | B2 | 8/2016 | Cheney |
| 9,498,259 | B2 | 11/2016 | Dirisio et al. |
| 9,510,879 | B2 | 12/2016 | Bottlang et al. |
| 9,579,135 | B2 | 2/2017 | Cook et al. |
| 9,700,361 | B2 | 7/2017 | Bottlang et al. |
| 9,763,713 | B2 | 9/2017 | Bottlang et al. |
| 9,788,863 | B2 | 10/2017 | Juchno et al. |
| 9,788,873 | B2 | 10/2017 | Bottlang et al. |
| 9,855,082 | B2 | 1/2018 | Hulliger et al. |
| 9,883,897 | B2 | 2/2018 | Taber |
| 9,924,987 | B2 | 3/2018 | Cheney |
| 10,022,168 | B2 | 7/2018 | Bottlang et al. |
| 10,070,905 | B2 | 9/2018 | Bottlang et al. |
| 10,092,336 | B2 | 10/2018 | Hess et al. |
| 10,123,831 | B2 | 11/2018 | Gephart |
| 10,159,514 | B2 | 12/2018 | Perrow et al. |
| 10,226,291 | B2 | 3/2019 | Perrow et al. |
| 2004/0039388 | A1 | 2/2004 | Biedermann et al. |
| 2004/0087955 | A1 | 5/2004 | Bordi |
| 2004/0116931 | A1 | 6/2004 | Carlson |
| 2004/0147928 | A1 | 7/2004 | Landry et al. |
| 2005/0004573 | A1 | 1/2005 | Abdou |
| 2005/0043732 | A1 | 2/2005 | Dalton |
| 2005/0203513 | A1 | 9/2005 | Jahng et al. |
| 2006/0167457 | A1 | 7/2006 | Suddaby |
| 2007/0055251 | A1 * | 3/2007 | Huebner ............ A61B 17/8047 606/279 |
| 2007/0213727 | A1 | 9/2007 | Bottlang et al. |
| 2008/0147124 | A1 | 6/2008 | Haidukewych et al. |
| 2008/0269753 | A1 | 10/2008 | Cannestra |
| 2009/0012571 | A1 * | 1/2009 | Perrow ............... A61B 17/1728 606/280 |
| 2009/0069812 | A1 | 3/2009 | Gillard et al. |
| 2010/0036430 | A1 | 2/2010 | Hartdegen et al. |
| 2010/0063505 | A1 * | 3/2010 | Frigg ................ A61B 17/8057 606/71 |
| 2011/0106182 | A1 | 5/2011 | Reisberg |
| 2011/0295324 | A1 | 12/2011 | Donley et al. |
| 2012/0296440 | A1 | 11/2012 | Choux et al. |
| 2013/0090695 | A1 | 4/2013 | Bernstein et al. |
| 2013/0190762 | A1 | 7/2013 | Frankle et al. |
| 2013/0304067 | A1 | 11/2013 | Hess et al. |
| 2014/0039630 | A1 | 2/2014 | Peyrot et al. |
| 2014/0066997 | A1 | 3/2014 | Humphreys |
| 2014/0128924 | A1 * | 5/2014 | Perrow ............... A61B 17/1671 606/287 |
| 2014/0188178 | A1 | 7/2014 | Juchno et al. |
| 2015/0157374 | A1 | 6/2015 | Gephart et al. |
| 2015/0230843 | A1 | 8/2015 | Palmer et al. |
| 2015/0238238 | A1 | 8/2015 | Cheney |
| 2015/0289918 | A1 | 10/2015 | Burckhardt et al. |
| 2015/0313656 | A1 | 11/2015 | Hulliger |
| 2016/0074082 | A1 | 3/2016 | Cremer et al. |
| 2016/0157905 | A1 | 6/2016 | Arellano et al. |
| 2016/0166296 | A9 | 6/2016 | Juchno et al. |
| 2016/0256203 | A1 | 9/2016 | Gephart |
| 2016/0270831 | A1 | 9/2016 | Perrow et al. |
| 2017/0360487 | A1 | 12/2017 | Moseley et al. |
| 2018/0000520 | A1 | 1/2018 | Juchno et al. |
| 2018/0036048 | A1 | 2/2018 | Bottlang et al. |
| 2018/0070997 | A1 | 3/2018 | Bottlang et al. |
| 2018/0078296 | A1 | 3/2018 | Hulliger et al. |
| 2019/0046247 | A1 | 2/2019 | Gephart |
| 2019/0175234 | A1 | 6/2019 | Perrow et al. |

OTHER PUBLICATIONS

Charlotte Claw Compression Plate, Wright Medical Technology, Inc., 2 pages, 2015.
F. Paris, V. Tarazona, E. Blasco, A. Canto, M. Casillas, J. Pastor, M. Paris, and R. Montero, Surgical stabilization of traumatic flail chest, Thorax (1975), 30, pp. 521-527.
Gephart, Matthew P., Bone Plate System, U.S. Appl. No. 62/692,464, filed Jun. 29, 2018.
Johnson Matthey Medical Components, How Does Nitinol Work? All About Nitinol Shape Memory and Superelasticity, retrieved on Jun. 21, 2018; http://jmmedical.com/resources/122/How-Does-Nitinol-Work%3F-All-About-Nitinol-Shape-Memory-and-Superelasticity.html; 2 pages.
International Search Report and Written Opinion dated Sep. 17, 2019, in corresponding International Application No. PCT/US2019/039263 (14 pages).
Extended European Search Report dated Mar. 17, 2022, in corresponding European Application No. 19824755.3 (7 pages).

* cited by examiner

BONE PLATE SYSTEM

CROSS-REFERENCE TO RELATED APPLICATION

This application claims benefit of U.S. Provisional Application No. 62/692,464, filed Jun. 29, 2018, which is hereby incorporated herein by reference in its entirety.

FIELD

The present disclosure relates to bone plate systems that are secured to bones and, more specifically, to bone plate systems for being secured to bones and compressing the bones together to facilitate fusion of the bones.

BACKGROUND

Bone plate systems are known for stabilizing bones. As used herein, the term "bone" refers to a whole bone or a portion of a bone. The bones stabilized by a bone plate system may be, for example, portions of a single bone such as a broken clavicle bone or separate vertebrae. One application of bone plate systems is to secure two or more vertebrae together with an intervertebral implant between the vertebrae. Another application of bone plate systems is to fuse portions of a bone that have been separated by a break or a cut. For example, a bone plate system may be used to facilitate fusion of portions of a broken bone of a clavicle, scapula, foot, or other extremity.

SUMMARY

In accordance with one aspect of the present disclosure, a bone plate system is provided that includes a bone plate having a plurality of elongated through openings. Each elongated through opening has a pair of end portions across the through opening from each other. The bone plate system includes a plurality of bone screws each having a head portion and a shank portion, the shank portion being configured to be driven into a bone. The bone plate system includes a plurality of sliders in the elongated through openings of the bone plate. Each slider has a throughbore configured to receive the head portion of one of the bone anchors. The sliders and bone screw head portions received therein are shiftable within the elongated through openings relative to the bone plate. The bone plate system includes at least one resilient member for being configured to apply a biasing force to each of the sliders to urge the slider toward one end portion of a respective through opening. Further, the bone plate system includes at least one actuator having an interference position in which the actuator inhibits shifting of the sliders toward the one end portion of the respective through opening. The at least one actuator also has a clearance position in which the actuator permits the at least one resilient member to urge the sliders and the bone screws received therein toward the one end portion of the through openings. In this manner, the bone plate system may be secured to bones and the at least one actuator moved from the interference position to the clearance position to cause the at least one resilient member to urge the sliders and bone screws along the elongated through openings and compress the bones together. Further, the bone plate is made of a rigid material such as titanium to resist post-surgical loading from the bones and keep the bones compressed together.

The present disclosure also provides a bone plate system for securing a pair of bones. The bone plate system includes a bone plate, elongated through openings of the bone plate, and a pair of bone screws for securing the bone plate to the bones. The bone plate system further includes a pair of sliders in the elongated through openings that each have a through bore for receiving a bone screw and at least one actuator configured to be clamped between the sliders and the bone plate. Further, the bone plate system includes at least one resilient member configured for applying a biasing force to the sliders to urge the sliders against the at least one actuator and cause the sliders to clamp the at least one actuator between the sliders and the bone plate. The at least one actuator is removable from being clamped between the sliders and the bone plate so that the biasing force urges each slider and the bone screw therein toward the other slider and bone screw for compressing the bones together. The bone plate system thereby provides a secure assembly of the at least one actuator clamped between the sliders and the bone plate which improves the ease of handling of the bone plate system during installation. Further, the at least one resilient member provides an easy-to-use approach for applying a biasing force against the bones by removing the at least one actuator from the bone plate.

In accordance with another aspect of the present disclosure, a method is provided for compressing a pair of bones. The method includes positioning a bone plate against bones and driving shanks of bone screws into through bores of sliders in elongated through openings of the bone plate and into engagement with the bones. The method includes removing at least one actuator from the bone plate and permitting at least one resilient member to urge the sliders and bone screw head portions therein toward each other along the elongated through openings of the bone plate and compress the bones together. In this manner, the method can be utilized to quickly secure the bone plate to the bones by driving the bone screws into through bores of the sliders and compress the bones by removing the at least one actuator from the bone plate.

DETAILED DESCRIPTION

Figure 1:
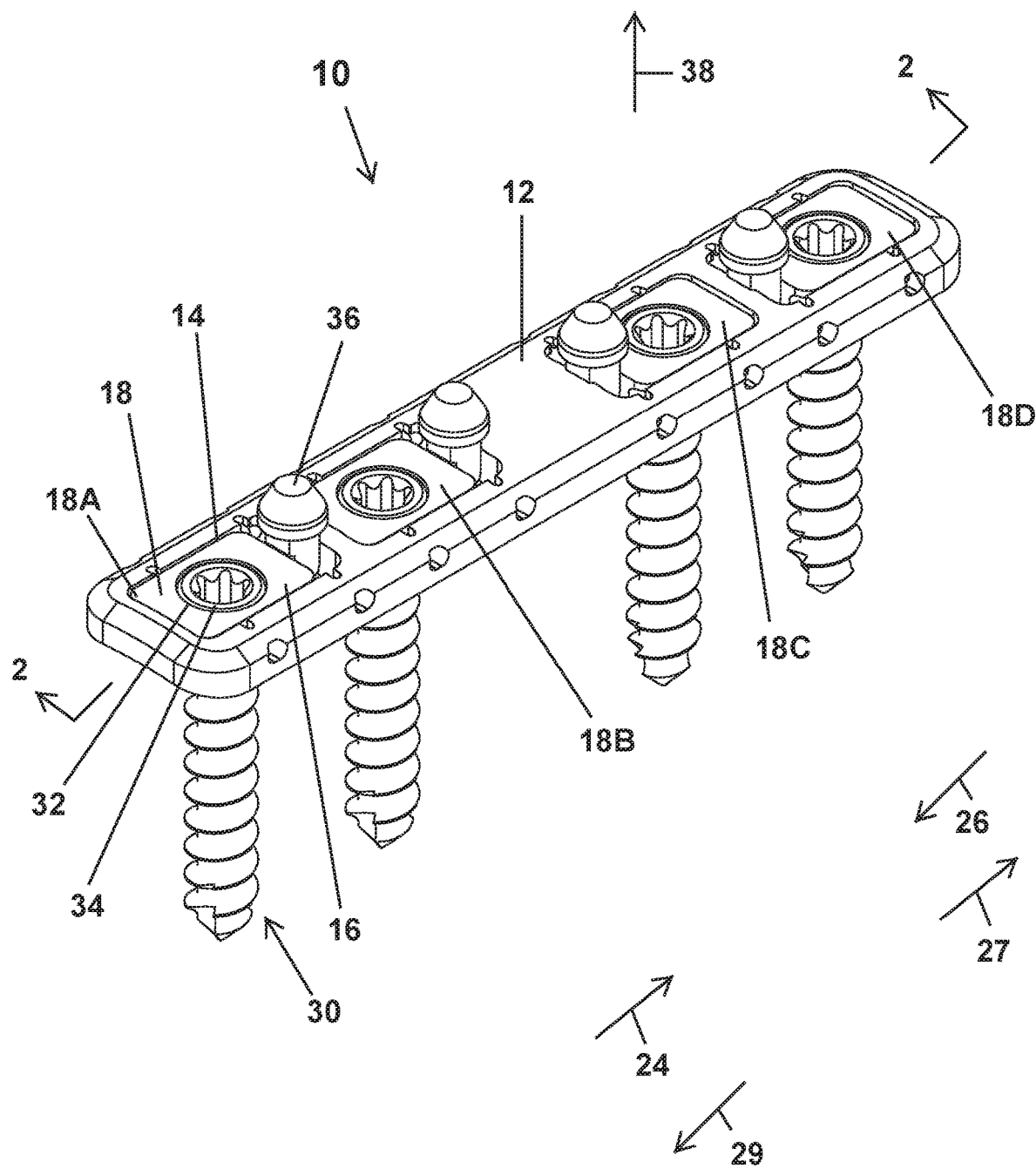
FIG. 1 is a perspective view of a bone plate system including a bone plate, slider assemblies in elongated through openings of the bone plate, bone screws in the slider assemblies, and removable spacers that keep the slider assemblies at one end of the through openings.

With reference to FIG. 1, a bone plate system 10 is provided that includes a bone plate 12 having one or more through openings 14 therein that receive one or more slider assemblies 16. The slider assemblies 16 each include a slider 18 and one or more resilient members such as wires 20, 22 (see FIG. 4). The wires 20, 22 have a loaded configuration wherein the wires 20, 22 apply a biasing force to the sliders 18 which urges each of the sliders 18 toward one end portion 64 (see FIG. 2) of the respective through opening 14. The bone plate system 10 also includes at least one actuator, such as spacers 36, which resist movement of the sliders 18 toward the one end portion 64 of the respective through opening 14 and keep the wires 20, 22 in a loaded configuration. Because the spacers 36 keep the wires 20, 22 in the loaded configuration, the wires 20, 22 have a preload that may be released by removing the spacers 36 from the through openings 14. The sliders 18 include sliders 18A, 18B for being secured to a first bone 86 (see FIG. 3) and sliders 18C, 18D for being secured to a second bone 84. The sliders 18 each include one or more through bores 32 that receive bone anchors such as bone screws 30.

Figure 5:
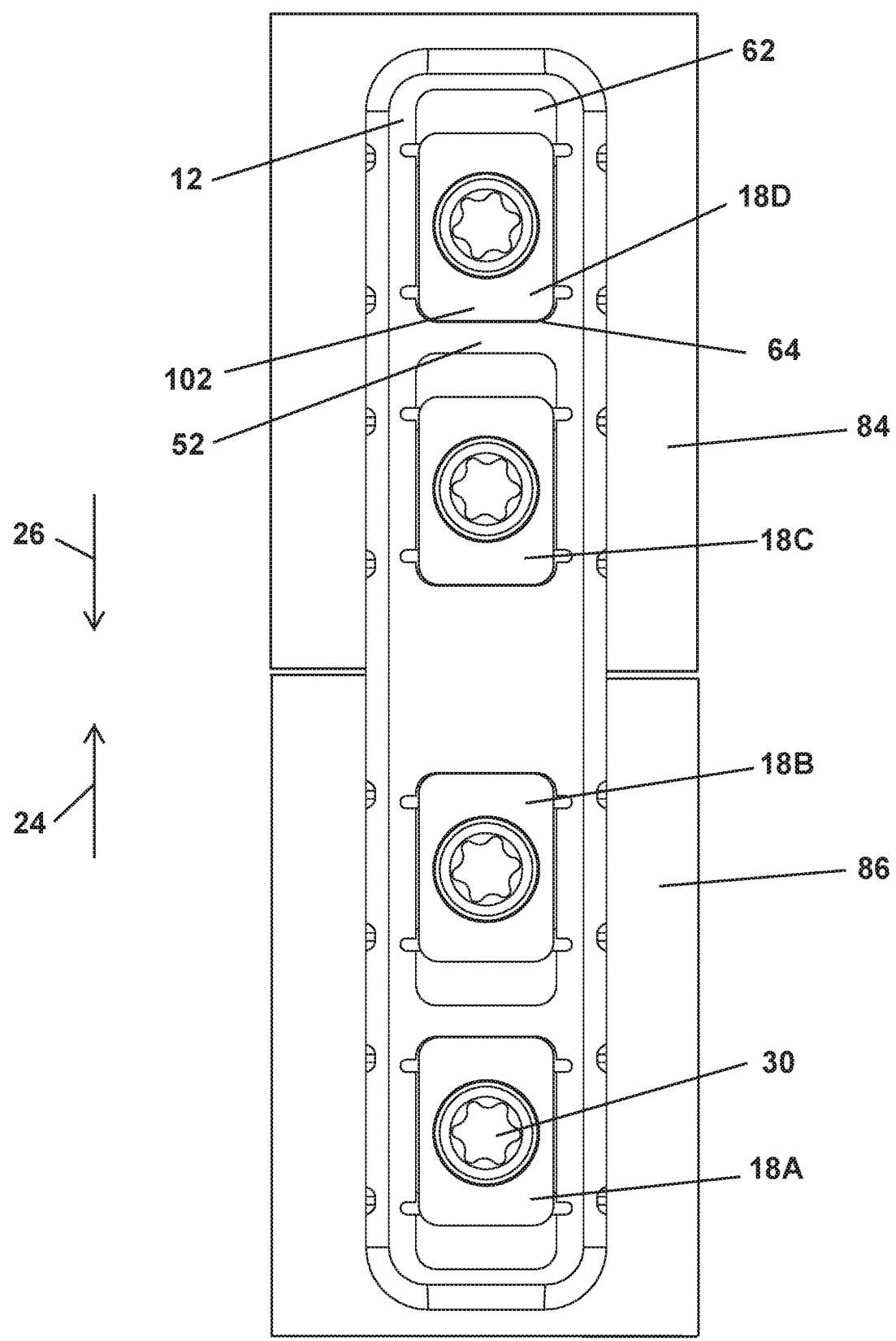
FIG. 5 is a view similar to FIG. 3 showing the spacers removed and the resilient wires having urged the sliders and bone screws received therein toward opposite ends of the elongated through openings which compresses the bones.

To install the bone plate system 10, the bone plate 12 is positioned against the bones 84, 86 and the bone screws 30 are driven into the through bores 32 of the sliders 18 and into the bones 84, 86 until head portions 34 of the bone screws 30 are seated in the through bores 32 of the sliders 18 as shown in FIG. 1. Next, a user operates the at least one actuator to cause the bone plate system 10 to compress the bones 84, 86. In one embodiment, the user operates the at least one actuator by removing the spacers 36 from the bone plate 12 generally in direction 38. Once the spacers 36 have been removed, the wires 20, 22 of the slider assemblies 16 can unload and urge the sliders 18A, 18B and bone screws 30 therein in direction 24 and urge the sliders 18C, 18D and bone screws 30 therein in direction 26. This compresses the bones 84, 86 together as shown in FIG. 5. Compressing the bones 84, 86 encourages fusion of the bones 84, 86 together or, in another embodiment, fusion of the bones 84, 86 together with a device therebetween such as an intervertebral implant between two vertebrae.

Figure 2:
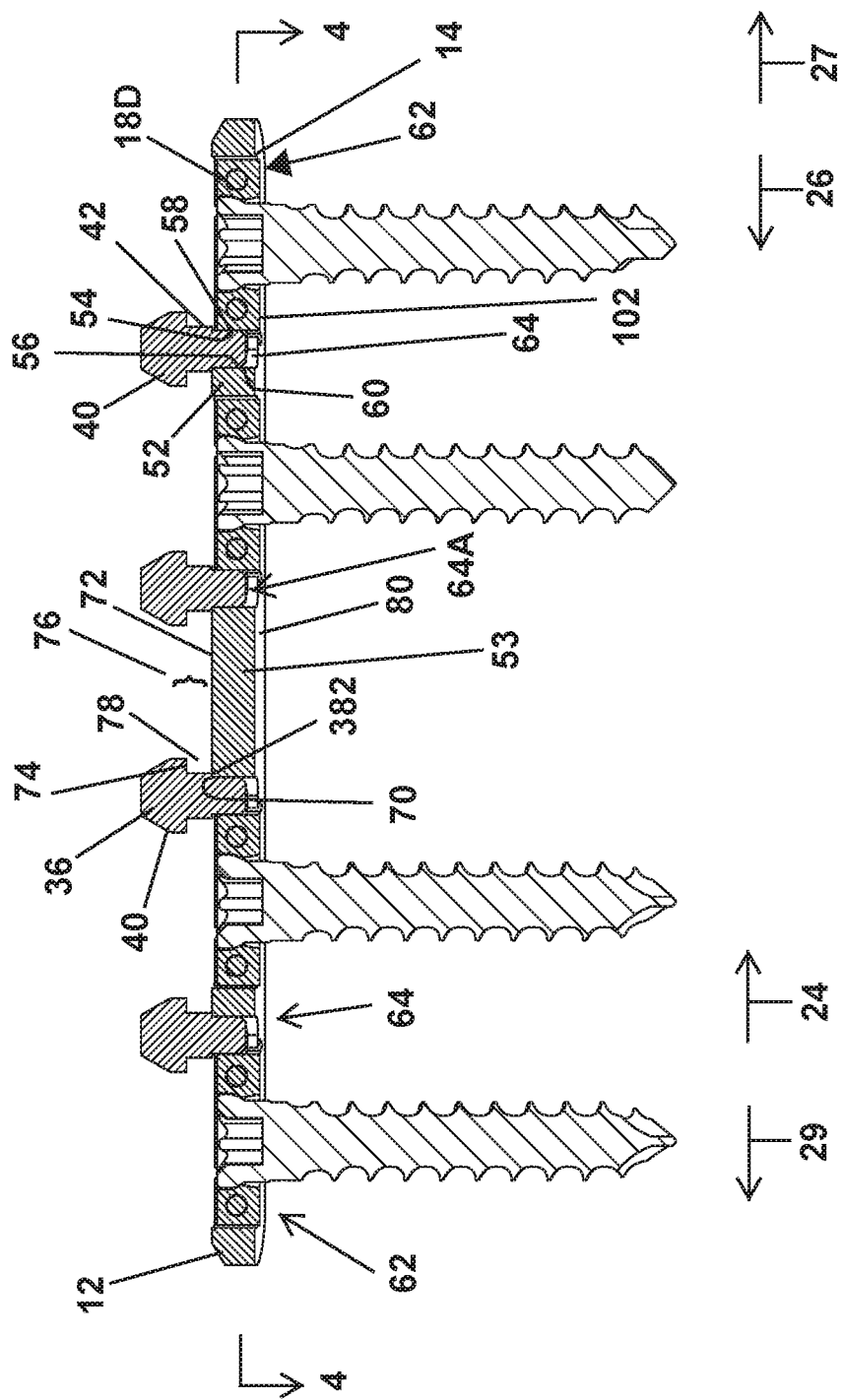
FIG. 2 is a cross-sectional view taken across line 2-2 of in FIG. 1 showing bodies of the spacers spacing sliders of the slider assemblies from walls of the bone plate.

With reference to FIG. 2, the spacers 36 each include a head 40 and a body 42. The head 40 is configured to be engaged by an actuator removal instrument such as spacer removal instrument 50 (see FIG. 19). With reference to the slider 18D, the body 42 of the spacer 36 is sized to extend into one of the through openings 14 and separate the slider 18D from a laterally extending wall 52 of the bone plate 12. More specifically, the body 42 includes flats 54, 56 with the flat 54 engaging a flat surface 58 of the slider 18D and the flat 56 engaging a flat surface 60 of the wall 52. With the spacer 36 connected to the bone plate 12, the presence of the spacer body 42 in the through opening 14 keeps the slider 18D at one end portion 62 of the through bore 32 and maintains the wires 20, 22 in a loaded configuration (see FIG. 4). The biasing force provided by the wires 20, 22 clamps the body 42 of the spacer 36 between the slider 18D and the wall 52 of the bone plate 12. By removing the spacers 36 from the bone plate 12, the wires 20, 22 can shift slider 18D in direction 24 toward an opposite end portion 64 of the through opening 14. The sliders 18A, 18B, 18C operate in a similar manner as discussed with respect to slider 18D.

The bone plate 12, sliders 18, and spacers 36 are made of rigid materials meaning that they are not intended to deform during normal installation and post-surgical use of the bone plate system 10. In one example, the bone plate 12, sliders 18, and spacers 36 are made of a metallic material such as titanium. The rigidity of the spacers 36 keeps the wires 20, 22 from being able to shift to the unloaded configuration thereof while the spacers 36 are present in the through openings 14.

The wires 20, 22 are made of a resilient material meaning that the wires 20, 22 are deformable and are able to recoil or spring back to shape after bending. Other resilient members may be used such as resilient members that recoil or spring back to shape after being stretched or compressed. The wires 20, 22 together apply a predetermined biasing force to the respective slider 18 such as in the range of approximately five pounds to approximately fifteen pounds, such as approximately ten pounds of force. The wires 20, 22 of the sliders 18 are also additive with the other levels of the bone plate 12 so that, with four sliders 18, the sliders 18 and bone screws 30 therein compress the bones 84, 86 with a compressive force of forty pounds.

In one example, the wires 20, 22 are made of a superelastic material. The superelastic material may be a metallic material such as superelastic nitinol. As an example, the wires 20, 22 may be made of superelastic nitinol and may each have a diameter of 0.028 inches. The bone plate system 10 utilizing these wires 20, 22 may provide 63 lbs of compressive force. The biasing force of the wires 20, 22 increases rapidly with relatively small increases in diameter. For example, the bone plate system 10 utilizing superelastic nitinol wires 20, 22 each having a diameter of 0.035 inches may provide 141 lbs of compressive force.

As used herein, the terms loaded configuration and unloaded configuration with reference to wires 20, 22 are relative terms wherein the wires 20, 22 are loaded or deformed more in the loaded configuration than in the unloaded configuration. Thus, when the wires 20, 22 are described as being in the unloaded configuration, it is not intended that the wires 20, 22 must be completely unloaded, just that the wires 20, 22 are less loaded or deformed than when the wires are in the loaded configuration.

Regarding FIG. 2, the spacer 36 is configured to facilitate removal of the spacer 36 by the spacer removal instrument 50. In one form, the spacer 36 includes a shoulder 70 that seats on an upper surface 72 of the bone plate 12. The shoulder 70 positions an underside surface 74 of the head 40 at distance 76 above the bone plate upper surface 72. The distance 76 creates a gap 78 of the bone plate 12/spacer 36 assembly into which a portion of the instrument 50 may fit and engage the underside surface 74 of the head 40. The bone plate 12 has a lower surface 80 opposite the upper surface 72 for being positioned against the bones 84, 86. The lower surface 80 may have a concave curvature to compliment the external surfaces of the bones 84, 86.

Figure 3:
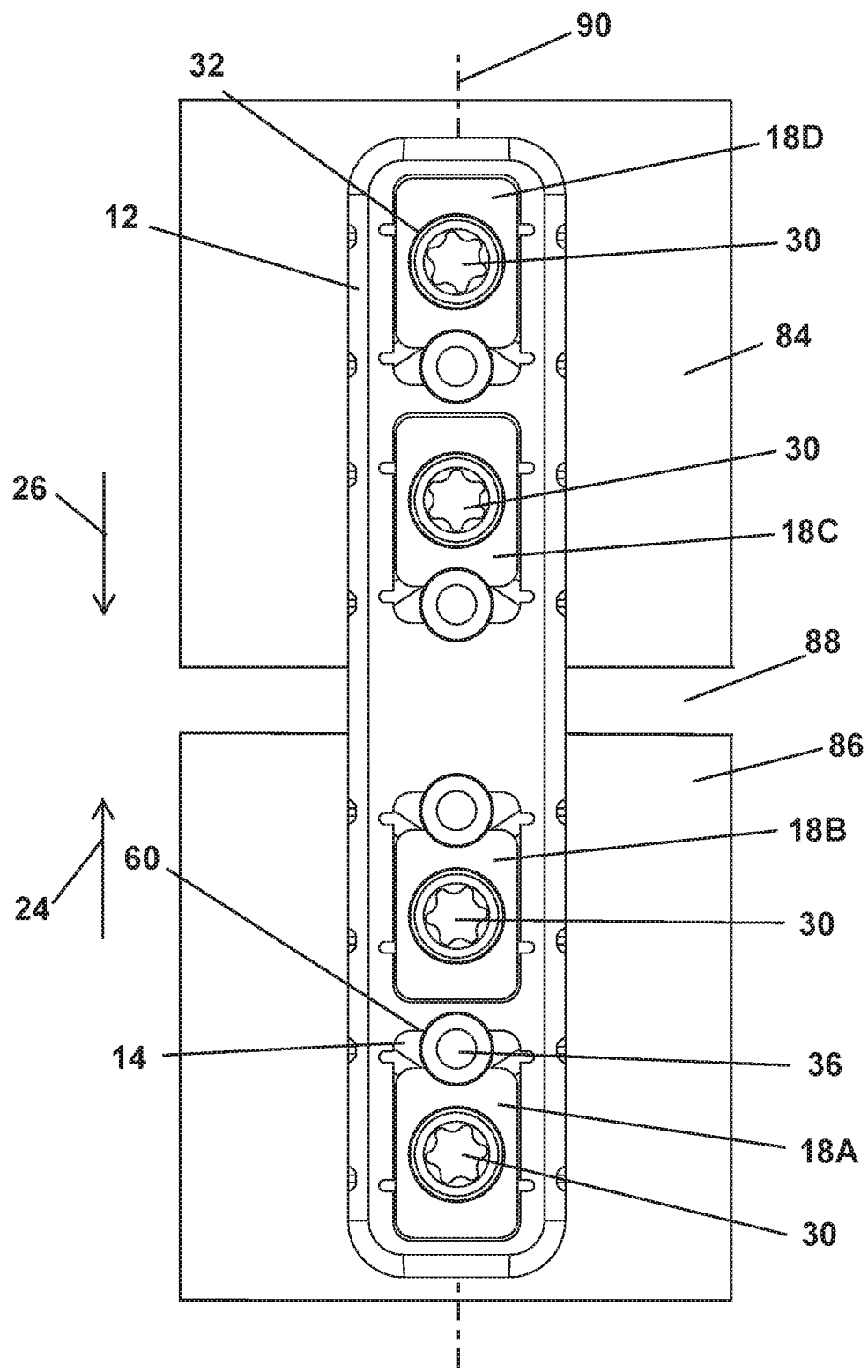
FIG. 3 is a top plan view of the bone plate system of FIG. 1 secured to bones having a gap therebetween.

With reference to FIG. 3, the bone plate 12 has been positioned against the bones 84, 86 which are separated by a small gap 88. The bone screws 30 have been driven into the through bores 32 of the sliders 18. In the embodiment of FIG. 3, the bone plate 12 has a longitudinal axis 90 and all of the sliders 18A, 18B, 18C, 18D are aligned along the longitudinal axis. This provides a small footprint for the bone plate 12 on the bones 84, 86 and is well suited for narrow bones such as bones of the clavicle, foot, or other extremities.

Figure 4:
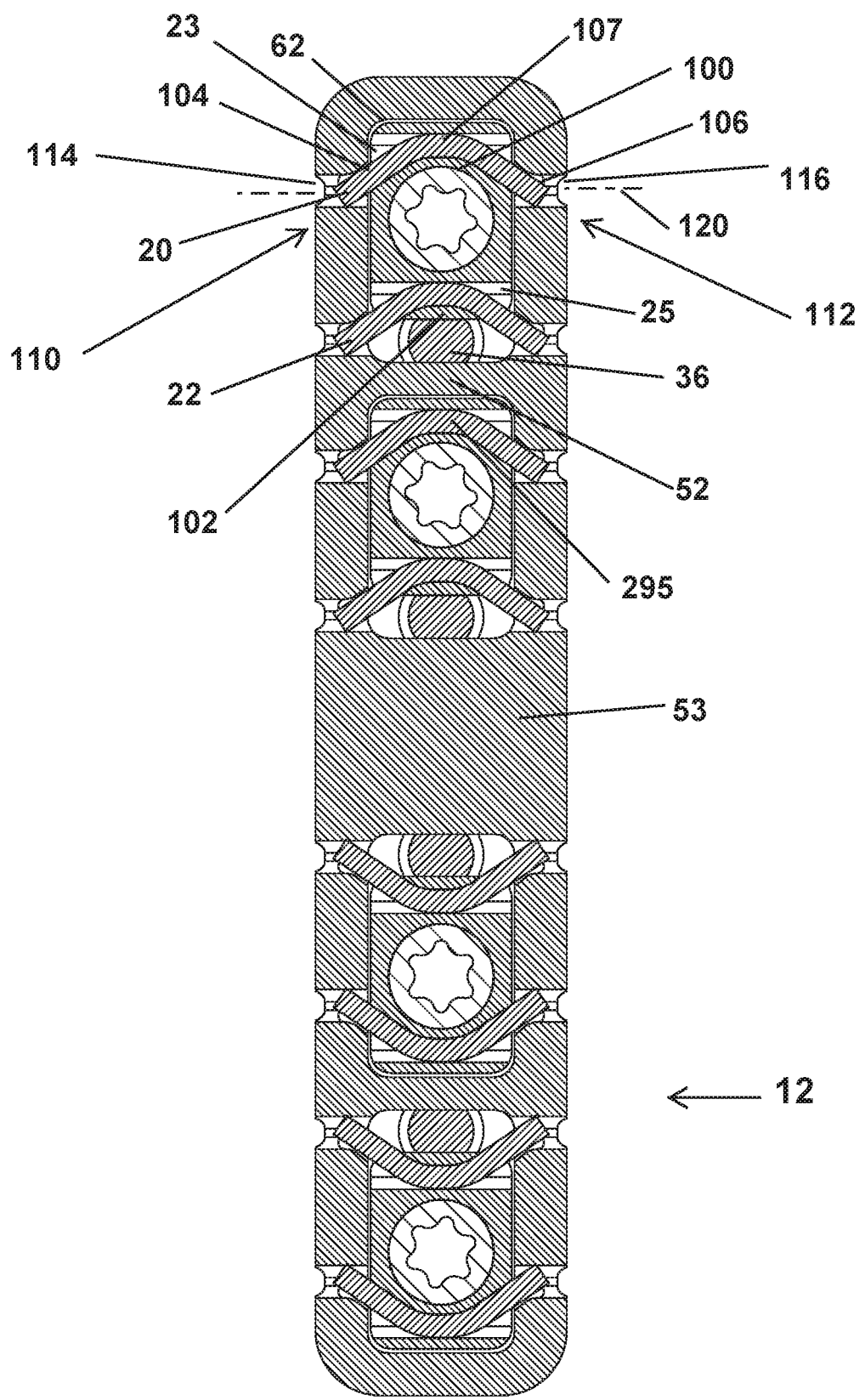
FIG. 4 is a cross-sectional view taken across line 4-4 in FIG. 2 showing resilient wires of the slider assemblies in a loaded configuration which clamps the spacers between the sliders and the bone plate.

With reference to FIG. 4, the spacers 36 are connected to bone plate 12 and hold the sliders 18 at the end portion 62 of the through openings 14. Because the sliders 18 are held at the end portion 62 of the through openings 14, the sliders 18 maintain the wires 20, 22 in the loaded configuration. The wires 20, 22 extend through passageways 23, 25 (see FIG. 8) of the sliders 18 and have a bent configuration around walls 100, 102 of the sliders 18. The wires 20, 22 each have an intermediate portion 107 secured to the slider 18. In one embodiment, the intermediate portion 107 is secured to the slider 18 such as by forming a dimple in an upper surface 109 (see FIG. 11) of an upper wall 111 of the slider 18 which deforms the upper wall 111 into engagement with the intermediate portion 107.

Regarding FIG. 4, the wires 20, 22 include end portions 104, 106 extending out of the passageways 23, 25 and are received in wire-receiving portions 110, 112 of the bone plate 12. The wire-receiving portions 110, 112 include pairs of apertures 114, 116 that receive wire end portions 104, 106. More specifically, the end portions 104, 106 of the wire 20 extend out of the passageway 23 and into apertures 114, 116 of the bone plate 12. Likewise, the end portions 104, 106 of the wire 22 extend out of the passageway 25 and into apertures 114, 116 of the bone plate 12. The wires 20, 22 support the sliders 18 in the through openings 14. The wires 20, 22 are made of a material and have a diameter sufficient to provide pull-through resistance for the sliders 18 such that the sliders 18 and bone screws 30 therein stay within the through openings 14 of the bone plate 12 despite loads applied to the bone screws 30 by the bones 84, 86.

With reference to FIG. 5, the spacers 36 have been removed from the bone plate 12 which permits the wires 20, 22 to unload by straightening. The unloading wires 20, 22 convert the preload or stored potential energy within the wires 20, 22 into biasing forces which shift the sliders 18A, 18B in direction 24 and sliders 18C, 18D in direction 26. The shifting of the sliders 18 in directions 24, 26 urges the bones 84, 86 together and removes the gap 88 therebetween. In one embodiment, the wires 20, 24 are able to shift the sliders 18 from the end portions 62 of the through openings 14 to the opposite end portions 64 of the through openings 14. Further, depending on patient anatomy, the wires 20, 24 may urge the sliders 18 less than the entire distance along the through openings 14. If the sliders 18 are spaced from the laterally extending walls of the bone plate 12 at the end portion 64 of the through opening 14, the wires 20, 22 will be bent and will continue to apply a biasing force to the sliders 18.

Figure 6:
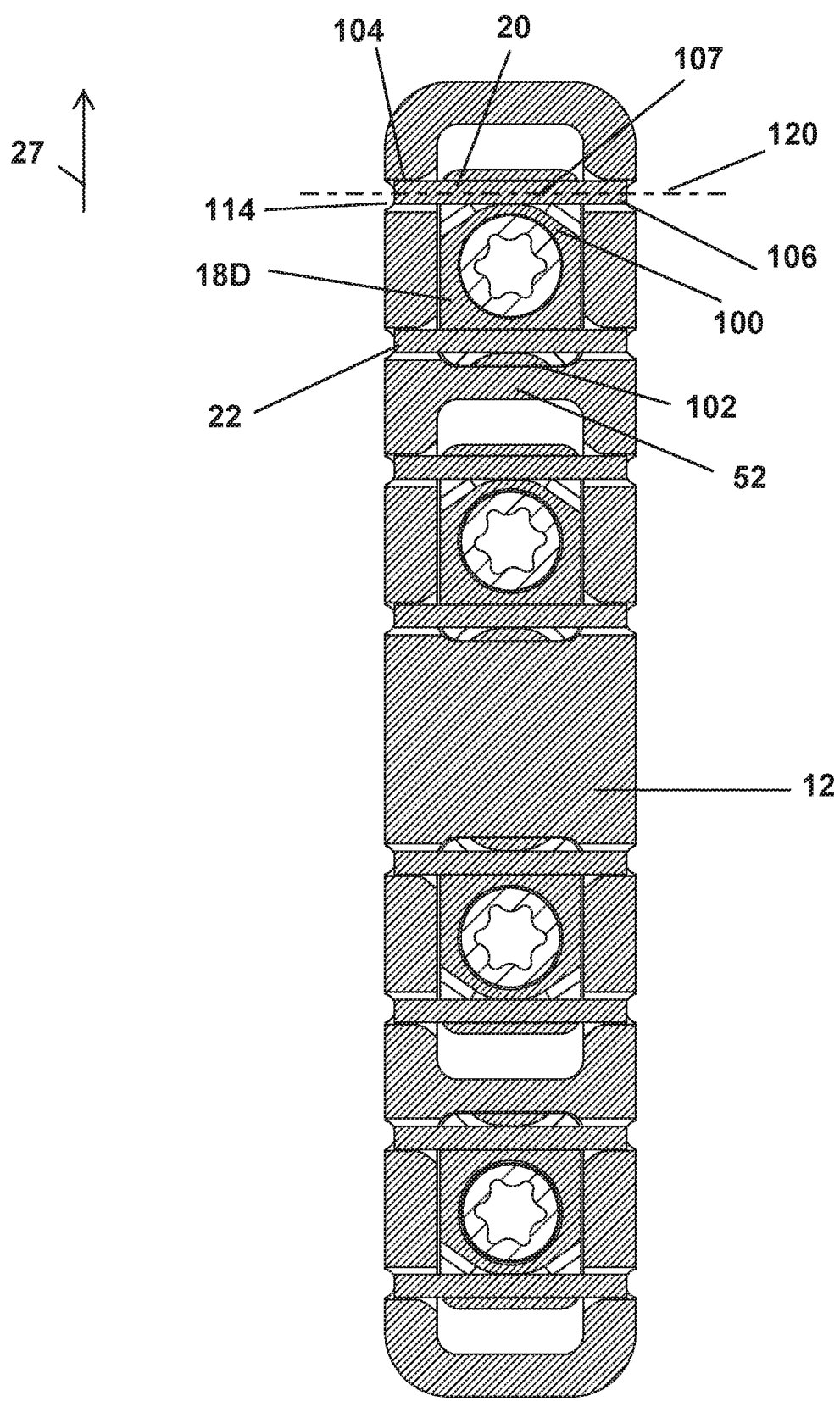
FIG. 6 is a cross-sectional view similar to FIG. 4 showing the resilient wires in an unloaded configuration after the spacers have been removed and the resilient wires have shifted the sliders toward the ends of the elongated through openings.

With reference to FIG. 6, the wires 20, 22 are shown in an unloaded configuration after the spacers 36 have been removed and the wires 20, 22 have urged the sliders 18 to the end portions 64 of the through openings 14. In the unloaded configuration, the wires 20, 22 are substantially straight with the end portions 104, 106 being generally coaxial with the intermediate portion 107. However, in other embodiments, the wires 20, 22 may still be bent in unloaded configuration such as if the patient's anatomy prevents the sliders 18 from shifting the full distance across the through openings 14. By comparing FIGS. 4 and 6, the end portions 104, 106 wiggle or pivot from a transversely extending orientation relative to each other to the coaxial orientation relative to each other as the wires 20, 22 shift from the loaded configuration to the unloaded configuration.

Figure 7:
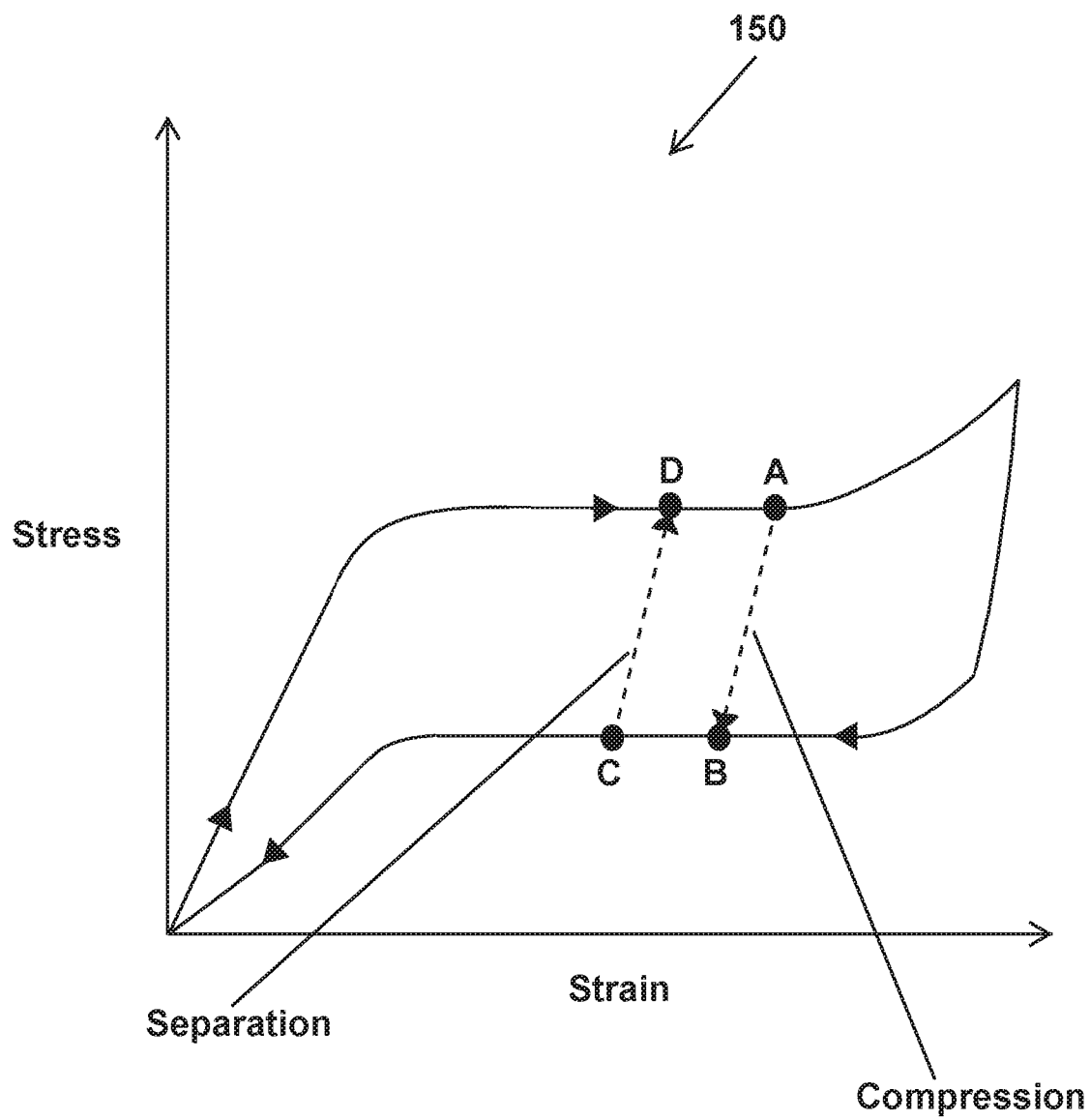
FIG. 7 is a stress-strain diagram of properties of superelastic nitinol.

With reference to FIG. 7, the wires 20, 22 may be made of a super-elastic material such as nitinol which has a stress-strain graph 150. The nitinol wires 20, 22 have a first characteristic (e.g. spring constant) when they are biasing the sliders 18 in directions 24, 26 (see FIG. 2) toward the end portions 64 of the through openings 14 such as after the spacers 36 are removed from the bone plate 12. However, the nitinol wires 20, 22 have a second characteristic (e.g. spring constant) that is different than the first characteristic when the sliders 18 are shifted in directions 27, 29 toward the end portions 62 of the through openings 14 such as if the bones 84, 86 are being urged apart due to patient movement. With reference to FIG. 1, the different first and second characteristics cause the wires 20, 22 to provide a greater resistance force to movement of the sliders 18A, 18B in direction 29 and sliders 18C, 18D in direction 27 than the force the wires 20, 22 apply against the sliders 18 to shift the sliders 18A, 18B in direction 24 and sliders 18C, 18D in direction 26. The higher resistance to shifting of the sliders 18 in directions 27, 29 causes the wires 20, 22 to act as one-way slide control mechanisms that effectively limit sliding movement of the sliders 18 to directions 24, 26 while inhibiting sliding movement of the sliders 18 in directions 29, 27.

The different characteristics of the nitinol wires 20, 22 may be due to the stress-induced formation of some martensite in the superelastic nitinol of the wires 20, 22 above the normal temperature of martensite formation. Because the martensite has been formed above its normal formation temperature, the martensite reverts immediately to underformed austenite as stress is removed. Austenite is higher strength than martensite and is stronger against bending of the nitinol wires 20, 22 back toward their loaded configuration.

For example, if the wires 20, 22 start at position A in graph 150 when bone plate system 10 is secured to the bones 84, 86, removing the spacers 36 allows the wires 20, 22 to shift the sliders 18 toward the end portions 64 of the through openings 14. The moving of the sliders 18 in the unloading direction releases stress in the wires 20, 22 and causes the stress and strain of the wires 20, 22 to move toward position B. As the sliders 18 further compress the bones 84, 86 together, the stress and strain of the wires 20, 22 moves to position C in stress-strain graph 150. However, if postsurgical patient movement imparts loading in direction 27 on the associated bone screw 30, the wires 20, 22 of the slider 18D resist this movement and the stress and strain within the wires 20, 22 jumps to position D in the stress-strain graph 150. The jump to the upper band of the stress-strain graph 150 indicates that the stress in the material is much higher which translates into greater resistance to bending of the wires 20, 22 back toward their loaded configuration.

Figure 8:
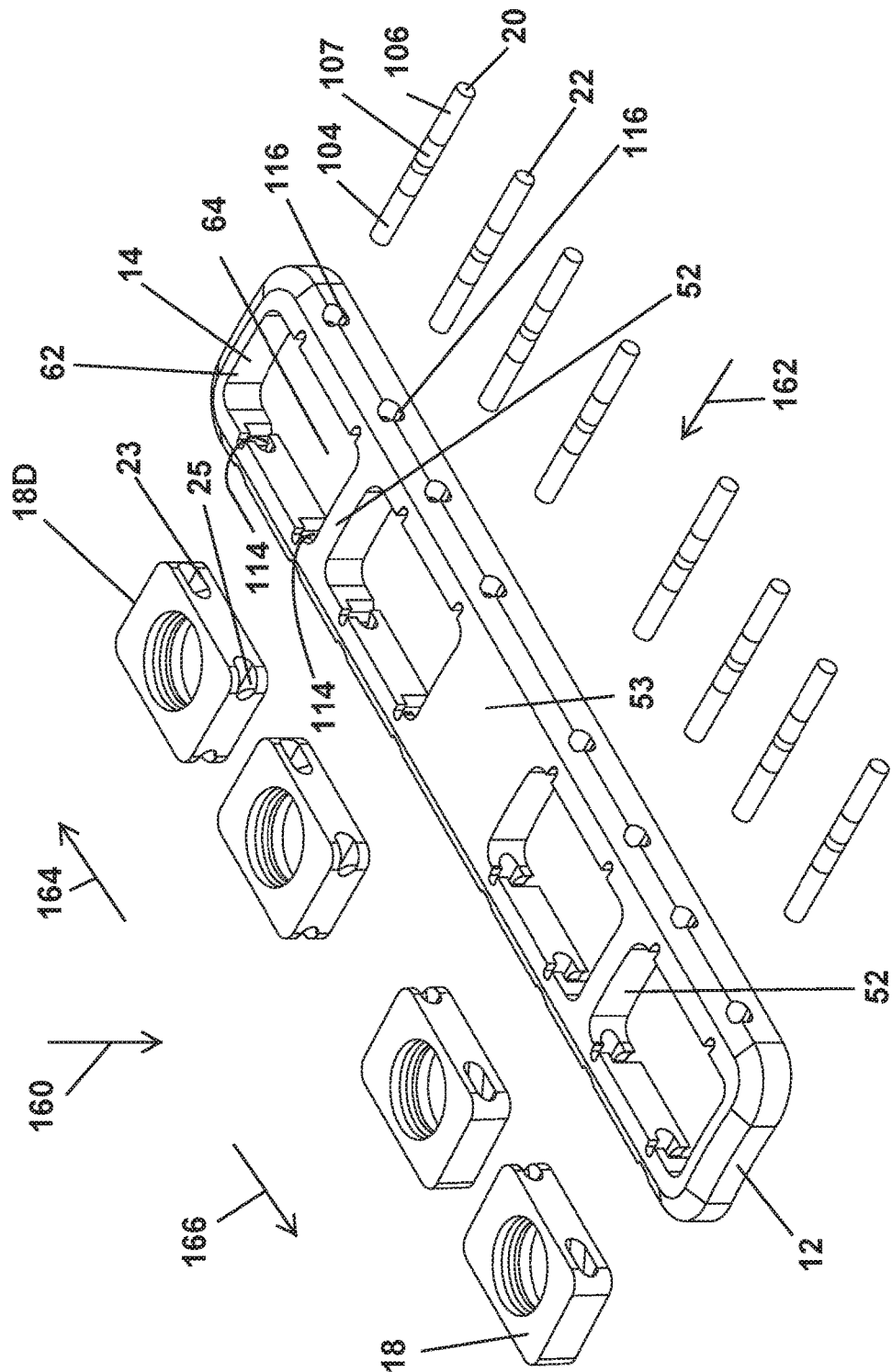
FIG. 8 is an exploded view of the bone plate system of FIG. 1 showing the bone plate, sliders, and resilient wires.

With reference to FIG. 8, the sliders 18 and wires 20, 22 of each slider are shown prior to assembly with the bone plate 12. During assembly, the sliders 18 are inserted in direction 160 into the through openings 14. The sliders 18 are positioned in their unloaded positions, i.e., at the end portions 64 of the through openings 14.

Next, the wires 20, 22 are provided in a straight, unloaded configuration. The end portions 104 of the wires 20, 22 are advanced in direction 162 through apertures 116 of the bone plate 12, through the passageways 23, 25 of the sliders 18, and into the through apertures 114 of the opposite side of the bone plate 12. The wires 20, 22 are thereby positioned so that the intermediate portion 107 of each wire 20, 22 extends through the respective passageway 23, 25, the end portion 104 of each wire 20 is received in one of the through apertures 114, and the end portion 106 of each wire 20, 22 is received in one of the through apertures 116.

The sliders 18 are then shifted in preloading directions 164, 166 toward the loaded positions thereof, i.e., toward end portions 62 (see FIG. 2) of the through openings 14. Shifting of the sliders 18 in the preloading directions 164, 166 loads or bends the wires 20, 22 and creates gaps 64A (see FIG. 2) between the sliders 18 and the laterally extending walls 52, 53 of the bone plate 12. The shifting of the sliders 18 in preloading directions 164, 166 may be performed by a technician utilizing a tool or an automated machine as some examples.

With reference to FIG. 8, to connect the spacers 36 to the bone plate 12, the spacers 36 are generally advanced in a direction 160 into the gaps 64A between the sliders 18 and the nearby bone plate laterally extending walls 52, 53 while the sliders 18 are held in the loaded position thereof by the technician or automated machine. Once the spacers 36 are positioned in the gaps 64A, the sliders 18 are released and the wires 20, 22 of each slider 18 urge the sliders 18 against the spacers 36 which clamps the spacers 36 between the sliders 18 and the laterally extending bone plate walls 52, 53. The process of shifting the sliders 18 to the loaded position and connecting the spacers 36 to the bone plate 12 may be performed on all of the sliders 18 at once, or may be performed on fewer than all of the sliders 18 (e.g., one or more) at a time.

Figure 9A:
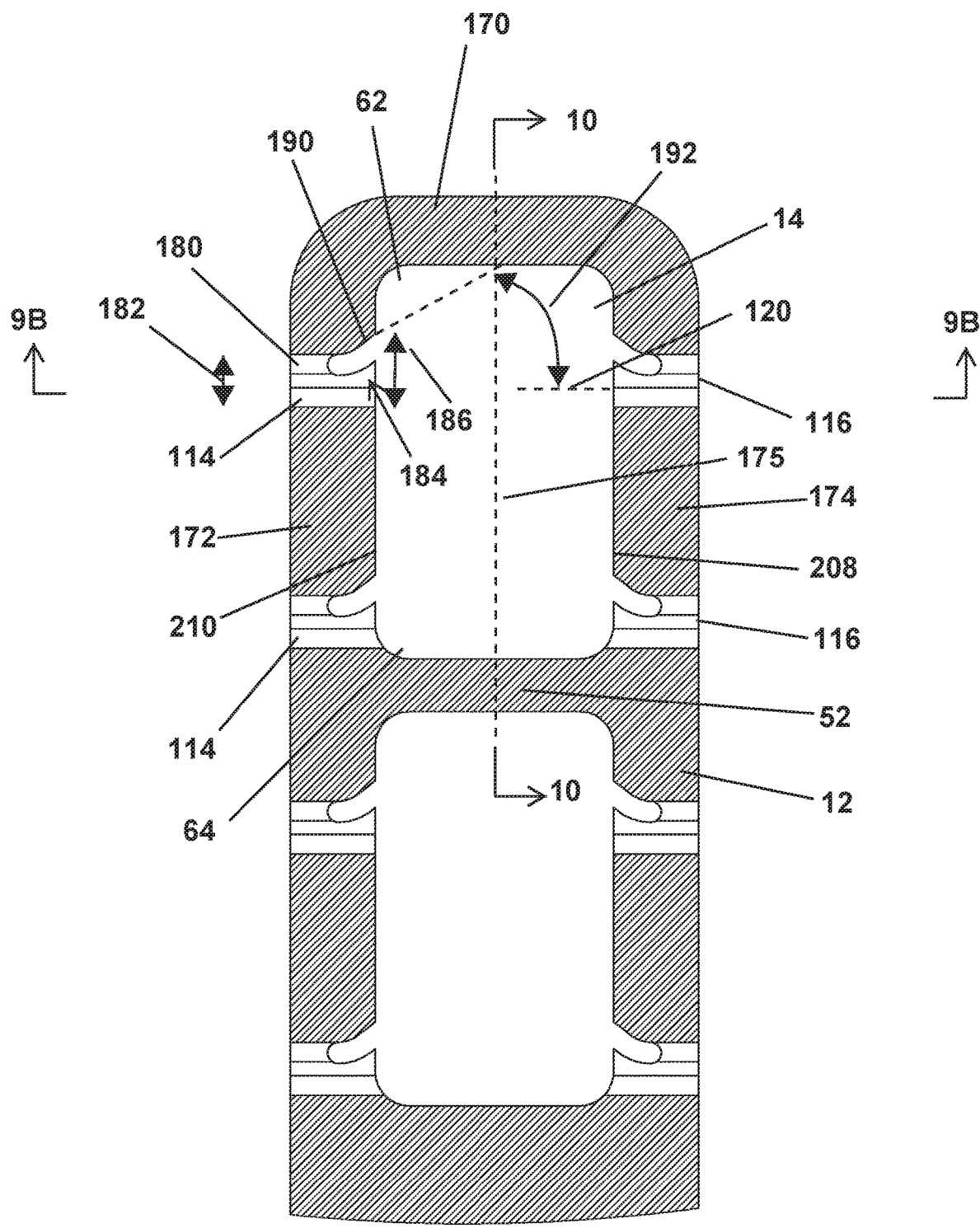
FIG. 9A is a cross-sectional view of the bone plate taken at one of the through openings of the bone plate.

Regarding FIG. 9A, the bone plate 12 includes an end wall 170 opposite the laterally extending wall 52 and side walls 172, 174 through which the apertures 114, 116 extend. The apertures 114, 116 have a varying profile throughout to accommodate the movement of the end portions 104, 106 of the wires 20, 22. Further, each through opening 14 has a longitudinal axis 175 extending between the end portions 62, 64 of the through opening 14. Although the following discussion refers to through aperture 114, it will be appreciated that the through aperture 116 is a mirror image of the through aperture 114 such that the following discussion also applies to through aperture 116, wire end portion 106, and side wall 174.

The through aperture 114 includes a narrow portion 180 having a distance 182 thereacross and an enlarged portion 184 having a distance 186 thereacross that is larger than the distance 182. The enlarged portion 184 provides clearance for the end portion 104 of the wire 20 to move from the oblique or transverse orientation thereof when the wires 20, 22 are in the loaded configuration (see FIG. 4) to the parallel or coaxial orientation when the wires 20, 22 are in the unloaded configuration thereof (see FIG. 6).

The side wall 172 also includes features that support the end portion 104 of the wires 20, 22 while minimizing stress imparted to the wires 20, 22. For example, the side wall 172 includes an angled surface 190 that extends at an acute angle 192 relative to an axis 120 extending laterally through the apertures 114, 116.

Figure 9B:
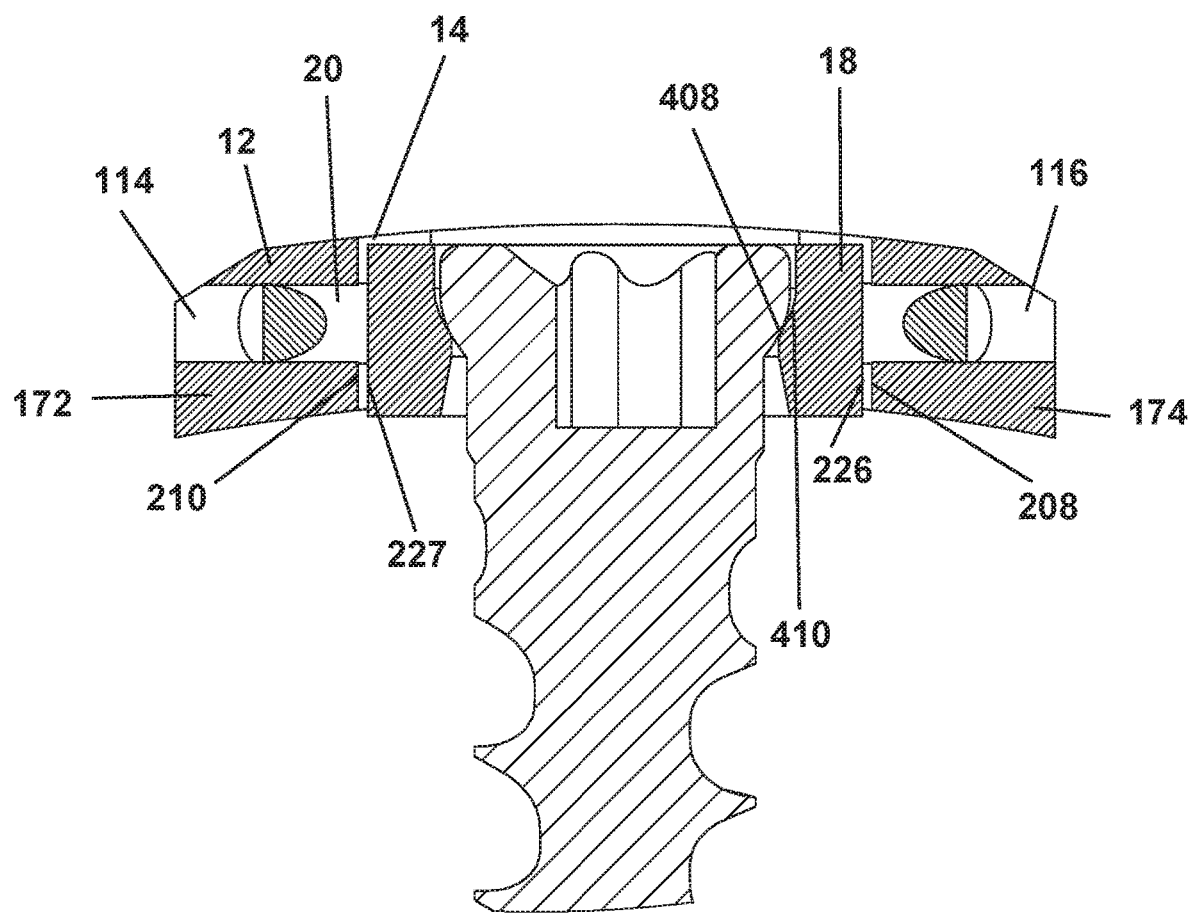
FIG. 9B is a cross-sectional view taken across line 9B-9B in FIG. 9A showing a slider in the through openings of the bone plate and a bone anchor received in a through bore of the slider.
Figure 11:
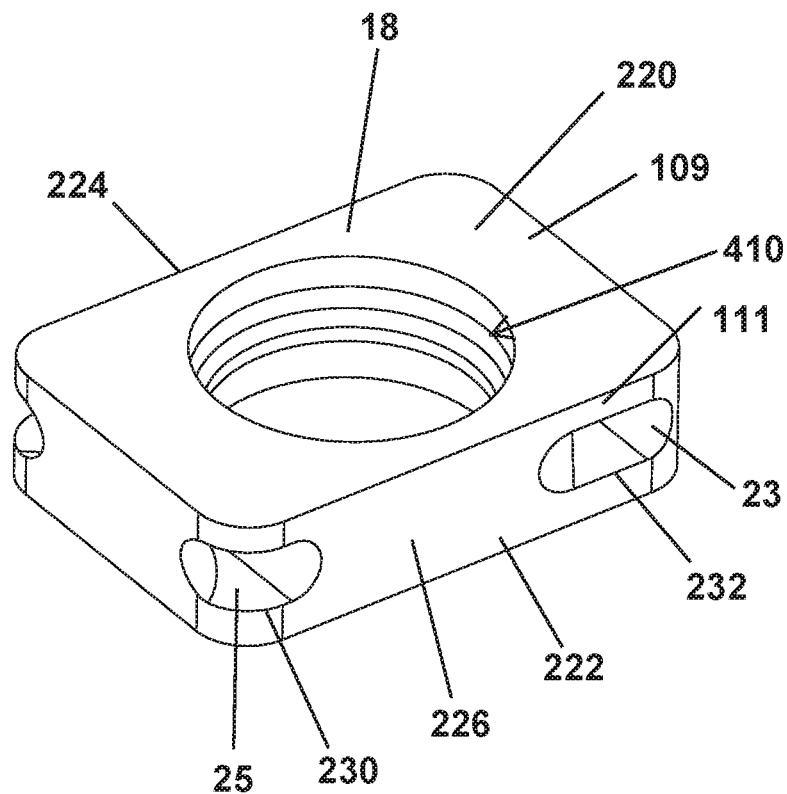
FIG. 11 is a perspective view of one of the sliders of FIG. 8 showing passageways of the slider that receive resilient wires.

With reference to FIGS. 9B and 11, the sliders 18 have a generally rectangular configuration and through openings 14 have a generally rectangular configuration that is longer than the sliders 18 to permit the sliders 18 and bone screws 30 therein to slide longitudinally within the through opening 14 along the bone plate 12. The slider 18 includes a body 220 having lateral sides 222, 224. The sides 222, 224 include flat surfaces 226, 227 for facing flat surfaces 208, 210 of the bone plate side walls 172, 174 as shown in FIG. 9B. The passageways 23, 25 of the slider 18 includes openings 230, 232 that open to the sides 222, 226 (see FIG. 14). The facing flat surfaces 208, 226 and 210, 227 of the sliders 18 and the bone plate 12 resist turning of the sliders 18 within the through openings 14.

Figure 10:
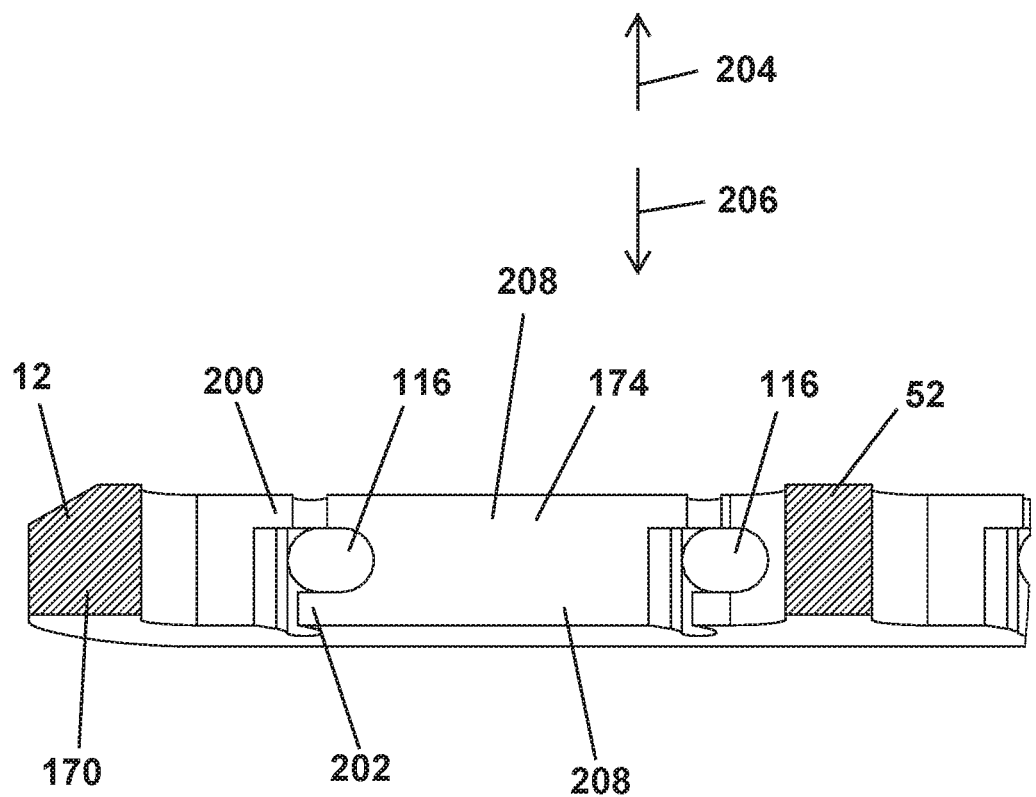
FIG. 10 is cross-sectional view taken across line 10-10 in FIG. 9A showing through apertures of a side wall of the bone plate that receive ends of the resilient wires.

Regarding FIG. 10, the side walls 172, 174 of the bone plate 12 include wall portions 200, 202 above and below the wires 20, 22 when the wires extend through the apertures 114, 116. The wires 20, 22 support the sliders 18 within the through openings 14 of the bone plate 12 against movement of the sliders 18 in directions 204, 205 out of the plane of the bone plate 12. The wires 20, 22 are made of a material and have an adequate diameter to be sufficiently strong in shear to resist the loading applied to the sliders 18 by the bone screws 30.

Figure 12:
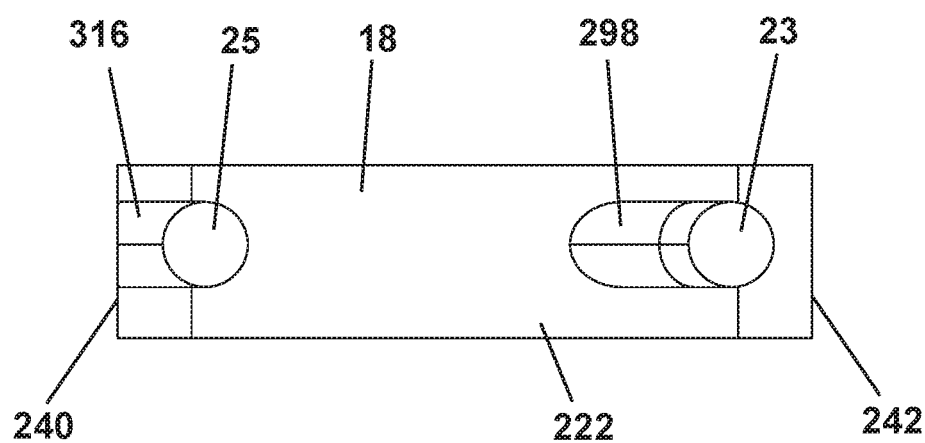
FIG. 12 is a side elevational view of the slider of FIG. 11 showing the passageways extending through the slider.

With reference to FIG. 12, the lateral sides 222, 224 of the slider 18 extend longitudinally between front and rear sides 240, 242. Further, the passageways 23, 25 extend through the slider 18 and include an angled surface 298 and a rounded surface 316 that lead into the passageways 23, 25 from the sides 222, 224.

Figure 13:
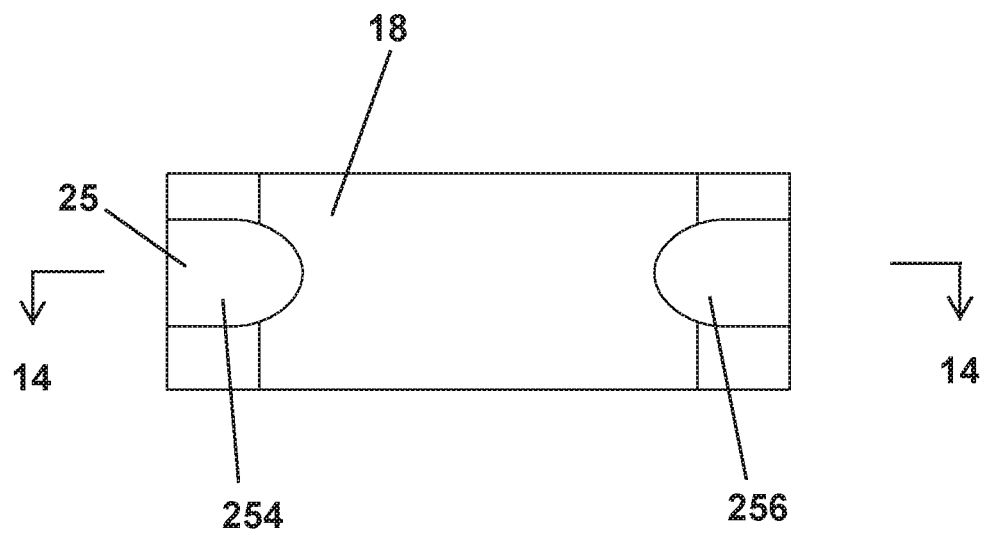
FIG. 13 is an end elevational view of the slider of FIG. 11 showing enlarged portions of one of the passageways of the slider that accommodate movement of portions of the resilient wire that extends through the passageway.
Figure 14:
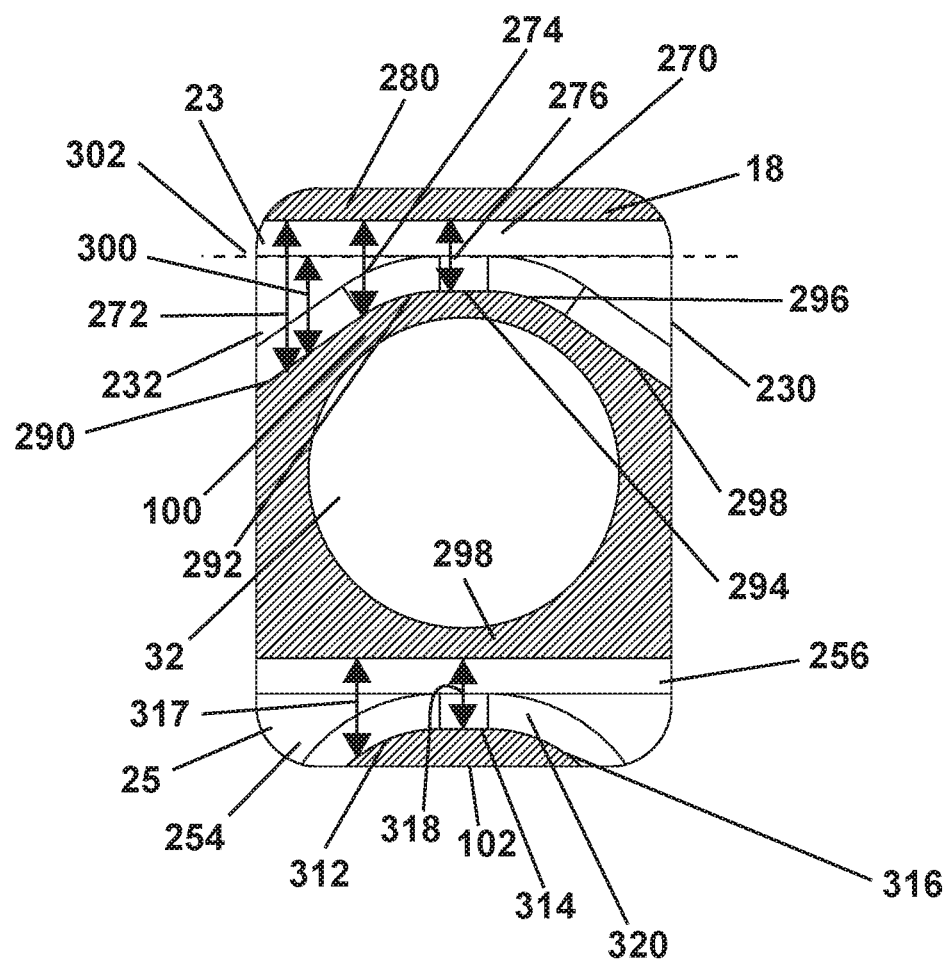
FIG. 14 is a cross-sectional view of the slider taken across line 14-14 in FIG. 13 showing the passageways of the slider having angled surfaces and curved surfaces to support the resilient wires in the loaded configuration thereof.

Turning to FIG. 13, the passageway 25 includes enlarged side portions 254, 256 for receiving the wire 22 and permitting the end portions 104, 106 space to pivot or wiggle as the wire 22 straightens toward the undeflected configuration thereof. With reference to FIG. 14, the passageway 23 of the slider 18 varies in size as the passageway 23 extends laterally across the slider 18 to provide support to the wire 20 when wire 20 is in deflected configuration thereof and provide clearance for the wire 20 as the wire 20 moves from the deflected configuration to the undeflected configuration. The passageway 23 includes enlarged side portions 232, 230 and an intermediate portion 270. The passageway 23 has a first distance 272 thereacross at the enlarged side portion 232, a second distance 274 thereacross intermediate the enlarged portion 232 and the intermediate portion 270, and a third distance 276 at the intermediate portion 270. The distance 272 is greater than the distance 274 which is in turn greater than the distance 276. Similar sizing exists at the enlarged side portions 230.

The slider 18 includes a wall 280 that abuts against or is a close proximity to a laterally extending wall of the bone plate 12 such as walls 52, 170 when the slider 18 is in the loaded position thereof. The slider 18 also includes the wall 100 extending around the through bore 32. The wall 280 may extend generally straight laterally across the slider while the wall 100 includes an angled surface 290, a rounded corner 292, an intermediate support surface 294, a rounded corner 296 and an angled surface 298 at the passageway 23. The angled surfaces 290, 298 each extend an angle 300 relative to the lateral axis 302 that extends straight through the passageway 23.

Similarly, the passageway 25 includes the enlarged side portions 254, 256 and a wall 102 extending generally laterally across the slider 18. The slider 18 also includes the wall 102 having a rounded surface 312, an intermediate support surface 314, and a rounded surface 316. The passageway 35 varies in size as the passageway 25 extends through the slider 18 including having a dimension 317 at the enlarged side portion 254 and a smaller distance 318 thereacross at an intermediate portion 320 of the passageway 25.

Figure 15:
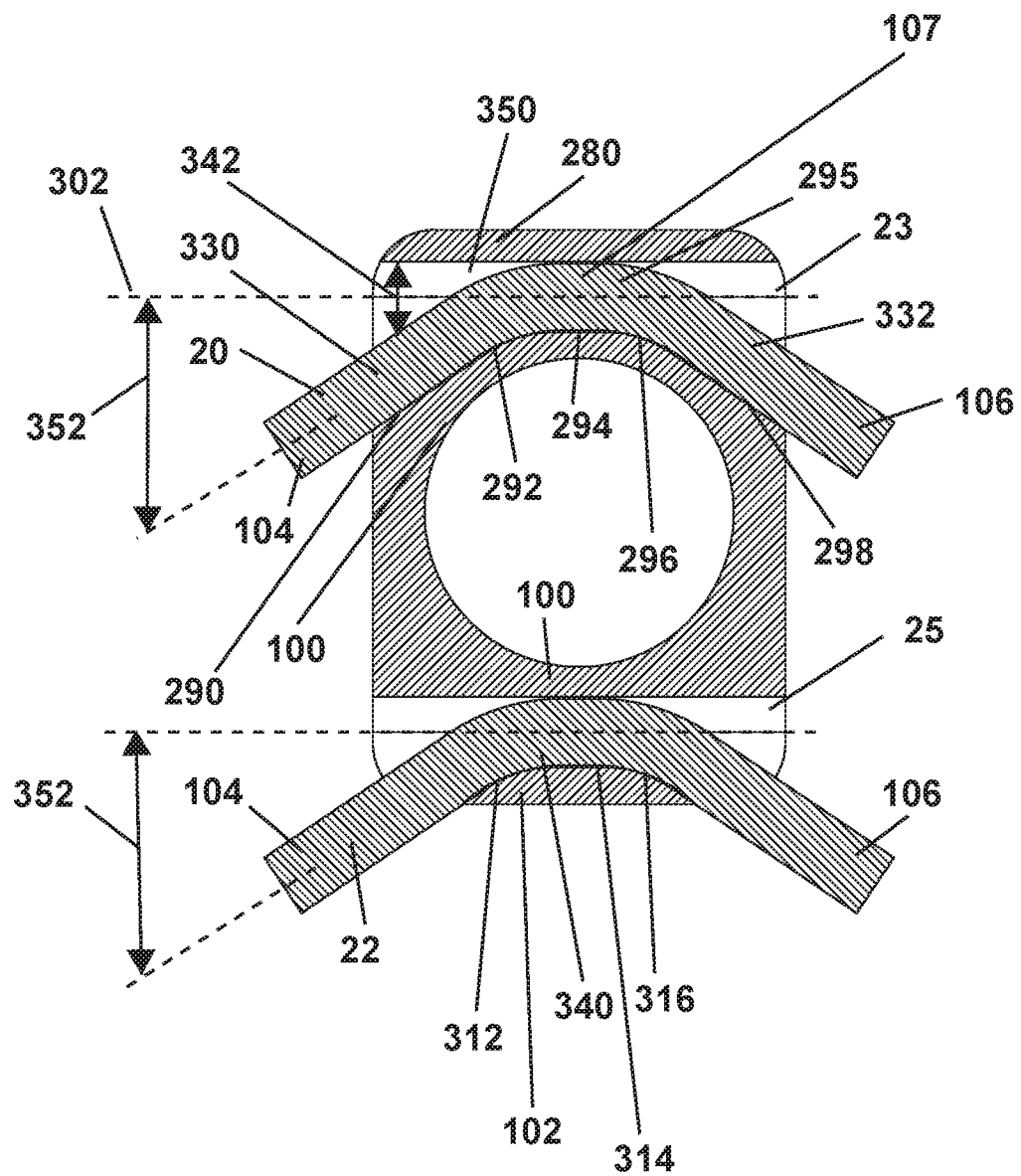
FIG. 15 is a cross-sectional view similar to FIG. 14 showing the resilient wires extending in the passageways of the slider and in the loaded configuration thereof with portions of the resilient wires extending along the angled surfaces and curved surfaces of the slider passageways.

FIG. 15 shows the wires 20, 22 in the deflected or loaded configuration thereof wherein the end portions 104, 106 of the wires 20, 22 extend outward from the lateral sides 222, 224 of the slider 18 for connecting to the bone plate 12. In the loaded configuration, the wires 20, 22 include outer intermediate portions 330, 332 that extend along and are supported by the angled surfaces 290, 298 and rounded surfaces 312, 316. The wires 20, 22 further include the intermediate portions 107, 340 that are supported, respectively, by the intermediate support surfaces 294, 314. Further, the rounded corners 292, 296 and rounded surfaces 312, 316 provide support without sharp corners which reduces stress in the wires 20, 22. Each wire 20, 22 generally has one bend 295 with a shape complimentary to the either the surfaces 292, 294, 296 or the surfaces 312, 314, 316. The walls 100, 102 of the slider 18 may thereby be configured to compliment a desired amount of bend 295 of the wires 20, 22 while limiting stress imparted to the wires 20, 22 supported by the walls 100, 102.

With the wires 20, 22 in the loaded configuration, the wires 20, 22 each extend at an angle 352 relative to the lateral axis 302 of the passageways 23, 25. The angles 352 may be the same or different depending on a particular application. With respect to the wire 20, the outer intermediate portion 330 is separated by a distance 342 from the wall 280 by a gap 350 which increases in size as the wire 20 extends away from the intermediate support surface 294 as shown in FIG. 15. The gap 350 provides clearance for the outer intermediate portion 330 to move once the spacer 36 have been removed from the bone plate 12 and the wire 20 can straighten out. The wire 22 likewise has a gap from the wall 100 that varies as the wire 22 extends laterally outward.

Figure 16:
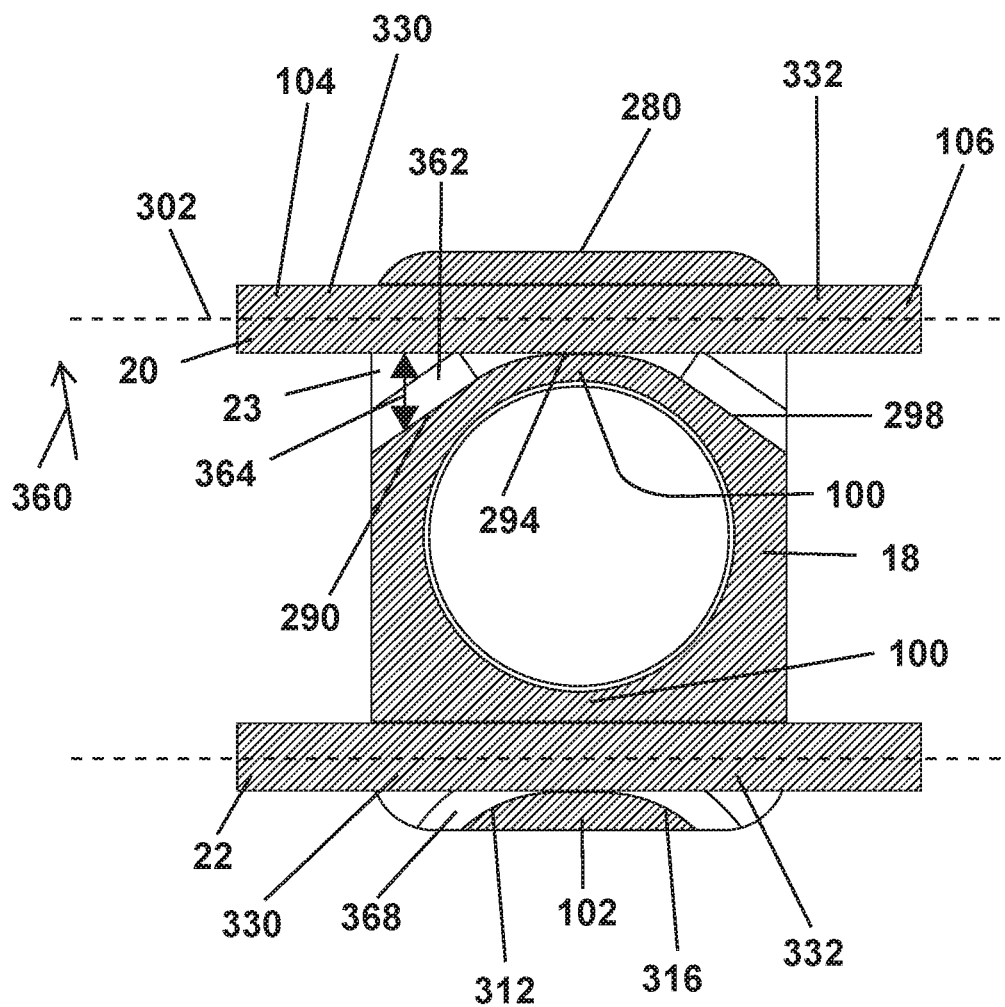
FIG. 16 is a cross-sectional view similar to FIG. 15 showing the resilient wires in an unloaded configuration wherein the portions of the resilient wires have pivoted to a straight configuration wherein the portions are spaced from the inclined surfaces and curved surfaces of the passageways.

With respect to FIG. 16, the wires 20, 22 are shown in the undeflected configuration such as after the spacer 36 has been removed from the bone plate 12. The outer intermediate portions 330, 332 of the wires 20, 22 pivot in direction 360 into contact with the wall 100, 280. This causes a gap 362 to separate the outer intermediate portions 330, 332 of the wire 20 from the angled surfaces 290, 298 of the wall 100 of the slider 18. The wire 20 is spaced from the wall 100 by a distance 364 that increases as the wire 20 extends laterally away from the intermediate support surface 294. Likewise, the outer intermediate portions 330, 332 of the wire 22 are spaced by a gap 368 from the curved surfaces 312, 316 of the wall 102.

Figure 17:
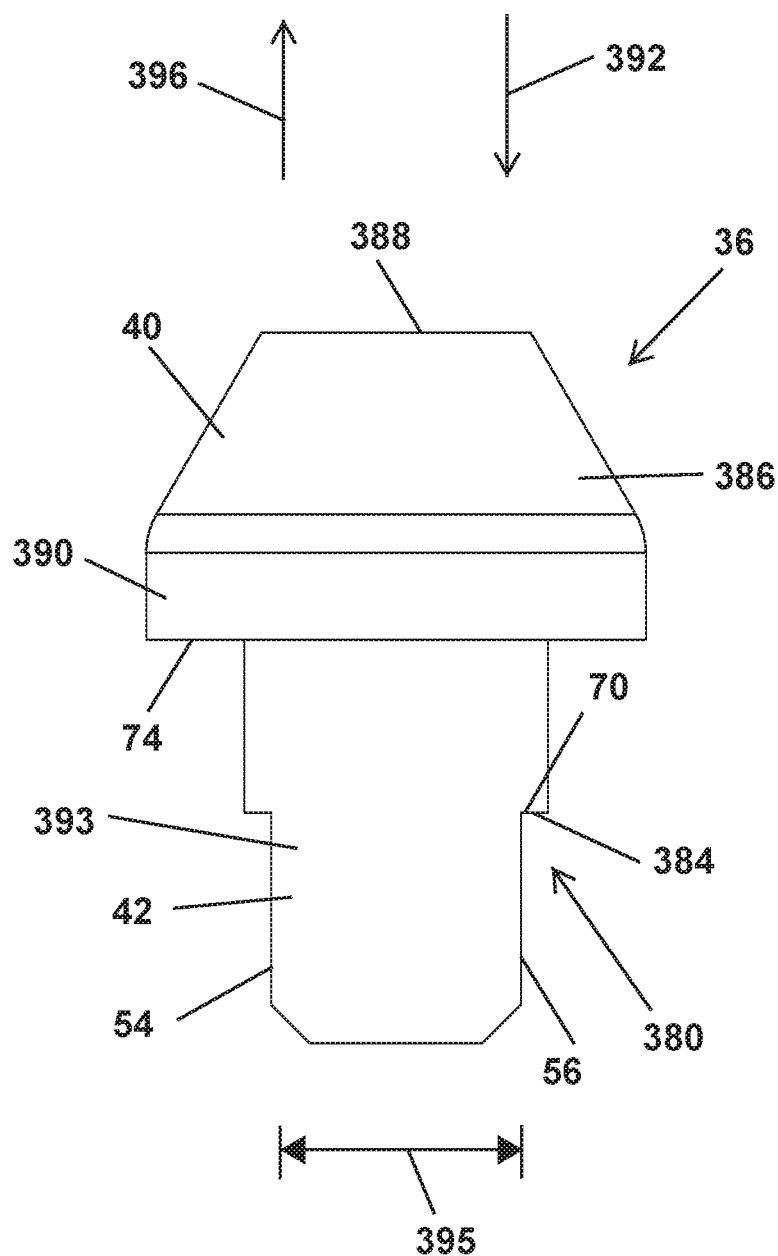
FIG. 17 is a side elevational view of one of the spacers of the bone plate system of FIG. 1 showing notches of the spacer that receive a slider on one side of the spacer and a wall of the bone plate on the other side of the spacer.

Regarding FIGS. 2 and 17, each shoulder 70 of the spacer 36 defines a notch 380 that receives a corner 382 of the bone plate 12 when the spacer 36 is connected to the bone plate 12. The shoulder 70 has a lower surface 384 that rests on the upper surface 72 of the bone plate 12. The head 40 has a tapered surface 386 that extends downwardly from a circular upper surface 388 to a cylindrical, radially outer surface 390 of the head 40. The surface 384 contacts the upper surface 72 of the bone plate 12 and the slider 18 and resist tilting or other movement of the spacer 36 which may lead to unintentional removal of the spacer 36 from the bone plate 12, such as during handling of the bone plate 12 prior to being placed at the surgical site. Further, the flats 54, 56 of the spacer 36 are normal to the biasing force and reactionary force imparted on the spacer 36 by the slider 18 and the bone plate 12 which facilitates secure clamping of the spacer 36 to the bone plate 12.

The tapered surface 386 is configured to cam resilient fingers 400 of the spacer removal instrument 50 (see FIG. 19) radially outward as the instrument 40 is connected to the spacer 36 and the resilient fingers 400 are advanced in direction 392 along the head 40. Once the resilient fingers 400 have advanced past the cylindrical surface 390, the resilient fingers 400 snap below the underside surface 74 of the head 40 of the spacer 36. With the resilient fingers 400 below the underside surface 74 of the head 40, the user may pull upward on the instrument 50 in direction 396 and withdraw the body 42 from between the slider 18 and the bone plate 12. The movement of the instrument 40 in direction 396 engages the resilient fingers 400 with the underside surface 74 of the head 40 and draws the spacer 36 out from the gap 64A between the slider 18 and the bone plate 12.

The body 42 of the spacer 36 includes a lower body portion 393 having a thickness 395 measured between the flats 54, 56. The thickness 395, in combination with the geometry of the slider 18 and bone plate 12, is selected to hold the wires 20, 22 in the loaded configuration with the maximum desired deformation in the wires 20, 22.

Figure 18:
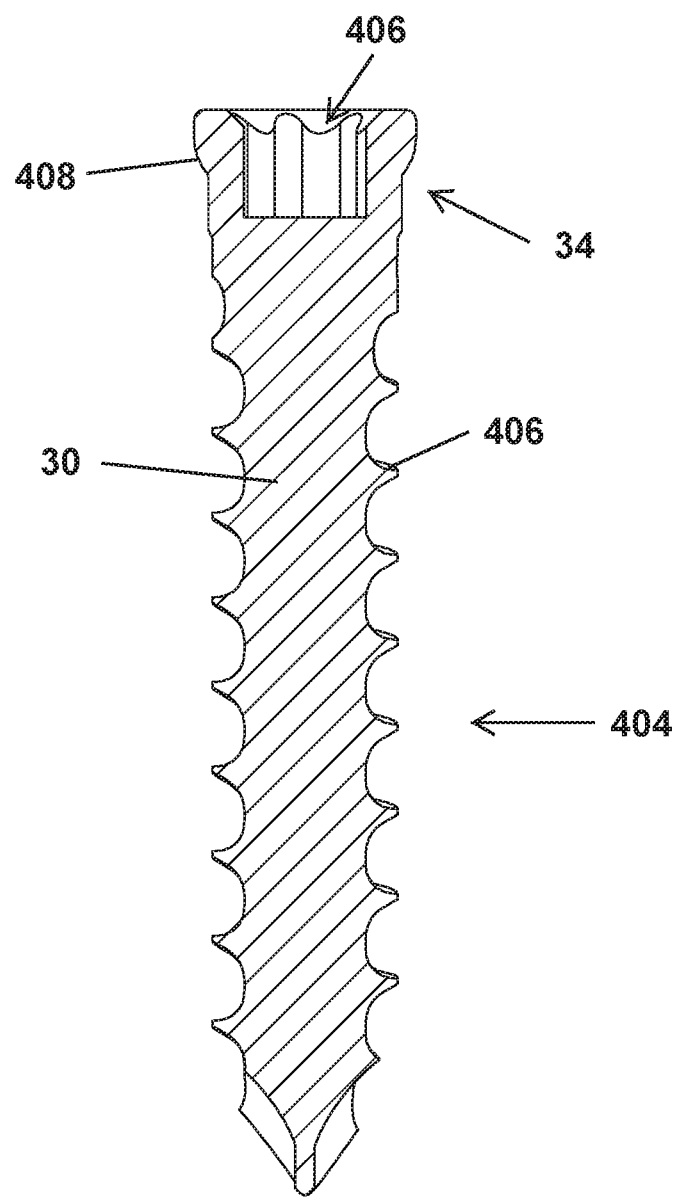
FIG. 18 is a cross-sectional view of one of the bone screws of the bone plate system of FIG. 1.

With reference to FIG. 18, the bone screws 30 each include the head portion 34 and a shank portion 404. The shank portion 404 includes threads 406 for driving into bone. In one embodiment, the shank portion 404 is configured to be self-tapping. The head portion 34 includes a rotary drive structure, such as a socket 406, that receives a screwdriver such as a hexa-lobed screwdriver. The head portion 34 further includes a curved lower surface 408 for engaging a seating surface 410 (see FIG. 9B) of the slider 18.

Figure 19:
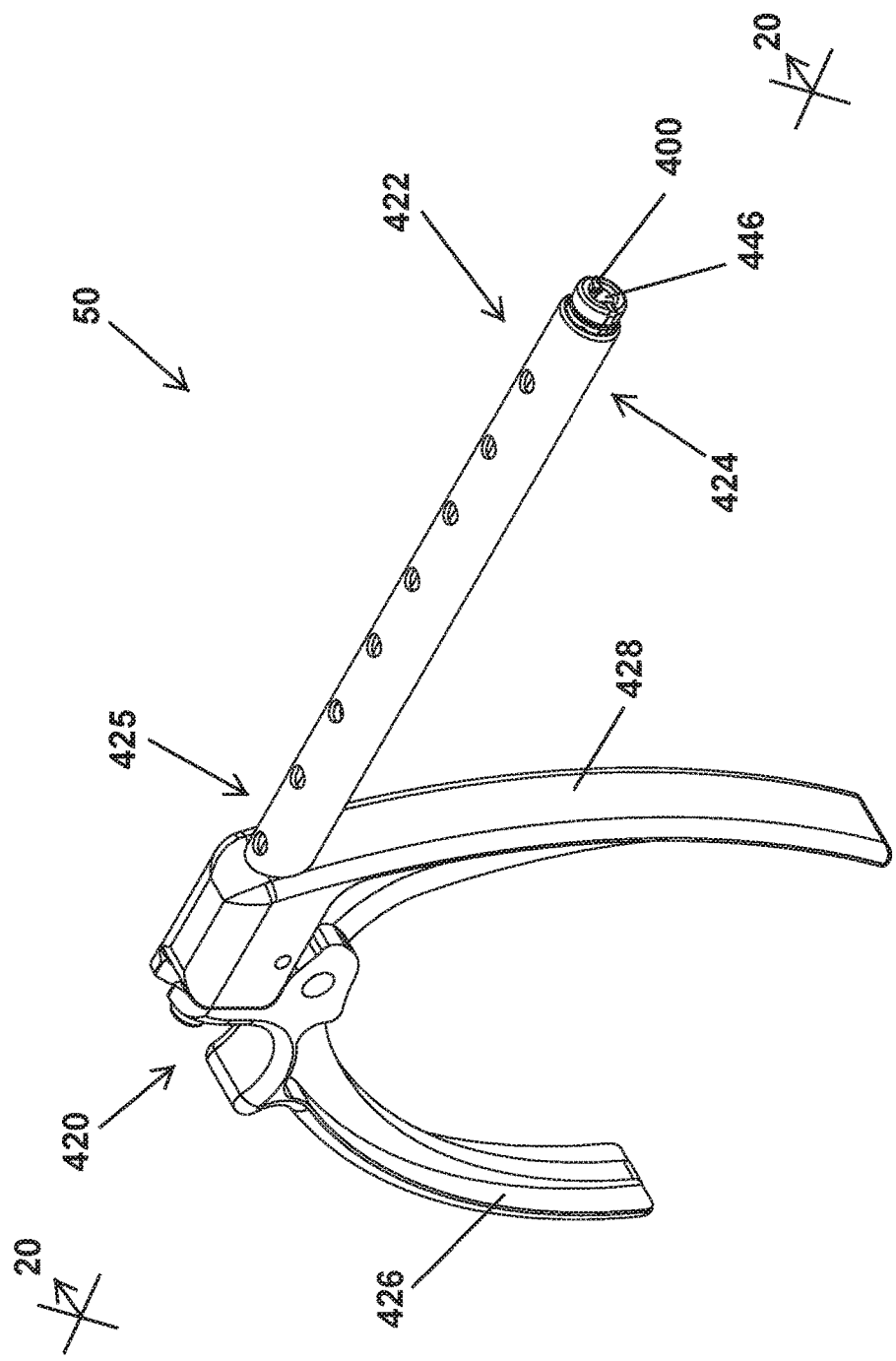
FIG. 19 is a perspective view of an instrument for removing the spacers of the bone plate system of FIG. 1.

With reference to FIG. 19, the spacer removal instrument 50 includes a handle assembly 420 and a shaft assembly 422. The shaft assembly 422 includes a distal end portion 424 configured to engage one of the heads 40 of the spacers 36 and a proximal end portion 425 connected to the handle assembly 420. The handle assembly 420 includes a stationary grip 428 and a handle 426 pivotally connected to the stationary grip 428 by a pin 429.

Figure 20:
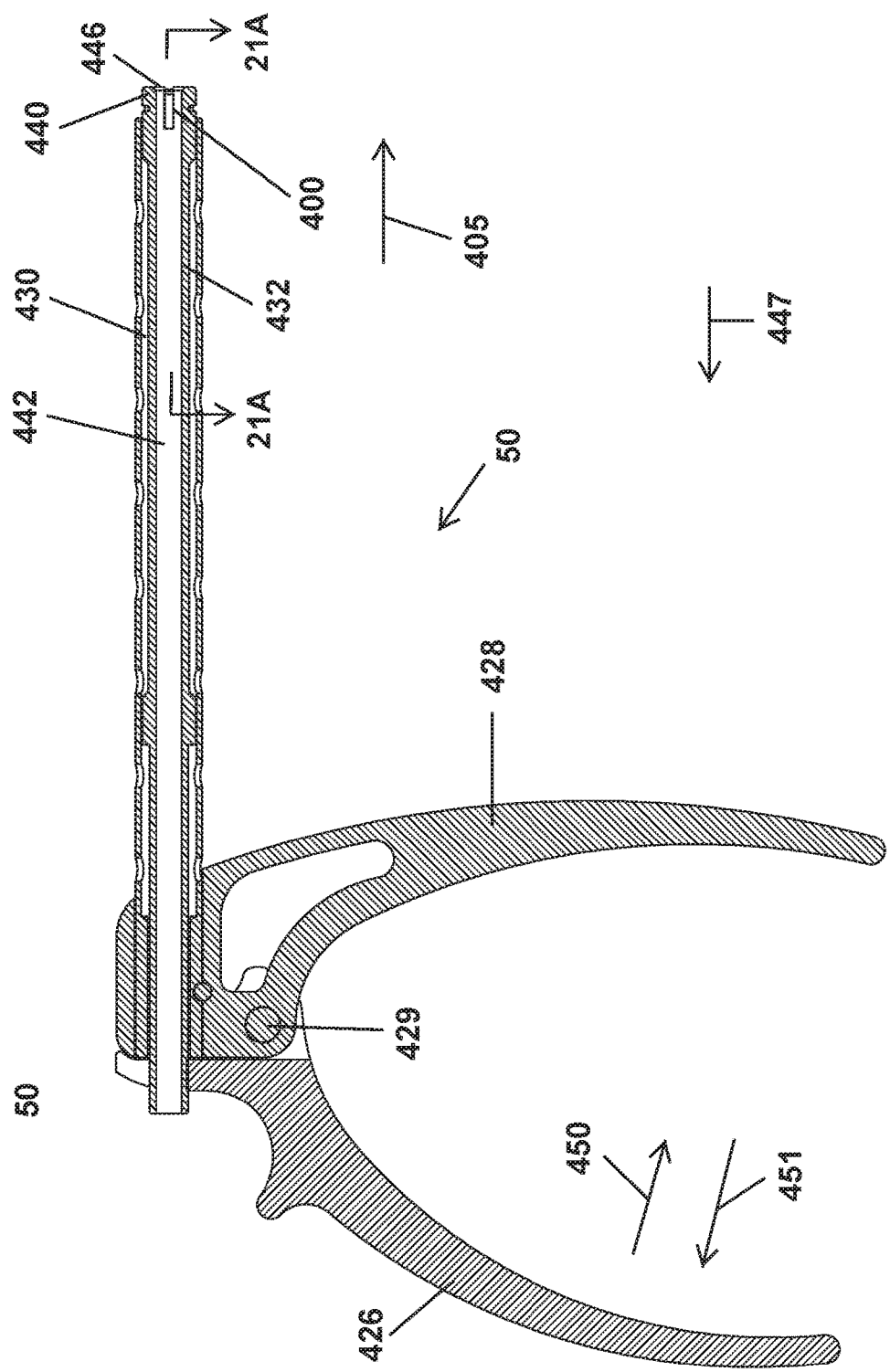
FIG. 20 is a cross-sectional view taken across line 20-20 in FIG. 19 showing an inner shaft of the instrument that is shiftable relative to an outer shaft of the instrument.

With reference to FIG. 20, the shaft assembly 422 includes an outer sleeve 430 mounted to the stationary grip 428 and an inner shaft 432 connected to the handle 426. The inner shaft 432 includes a rim 440 having the one or more resilient fingers 400 mounted thereto. The resilient fingers 400 are mounted to the inner shaft 432 with pins that extend through openings 441 (see FIG. 21A) of the resilient fingers 411. In another embodiment, the inner shaft 432 and the one or more resilient fingers 400 have an integral construction rather than being assembled. The inner shaft 432 also includes a cannula 442 for holding the spacers 36 in a line within the cannula 442 as the spacers 36 are removed one by one from the bone plate 12. In another embodiment, the grip 428 may be movable and the handle 426 may be fixed or both the grip 428 and the handle 426 may be movable to operate the instrument 50.

Figure 21A:
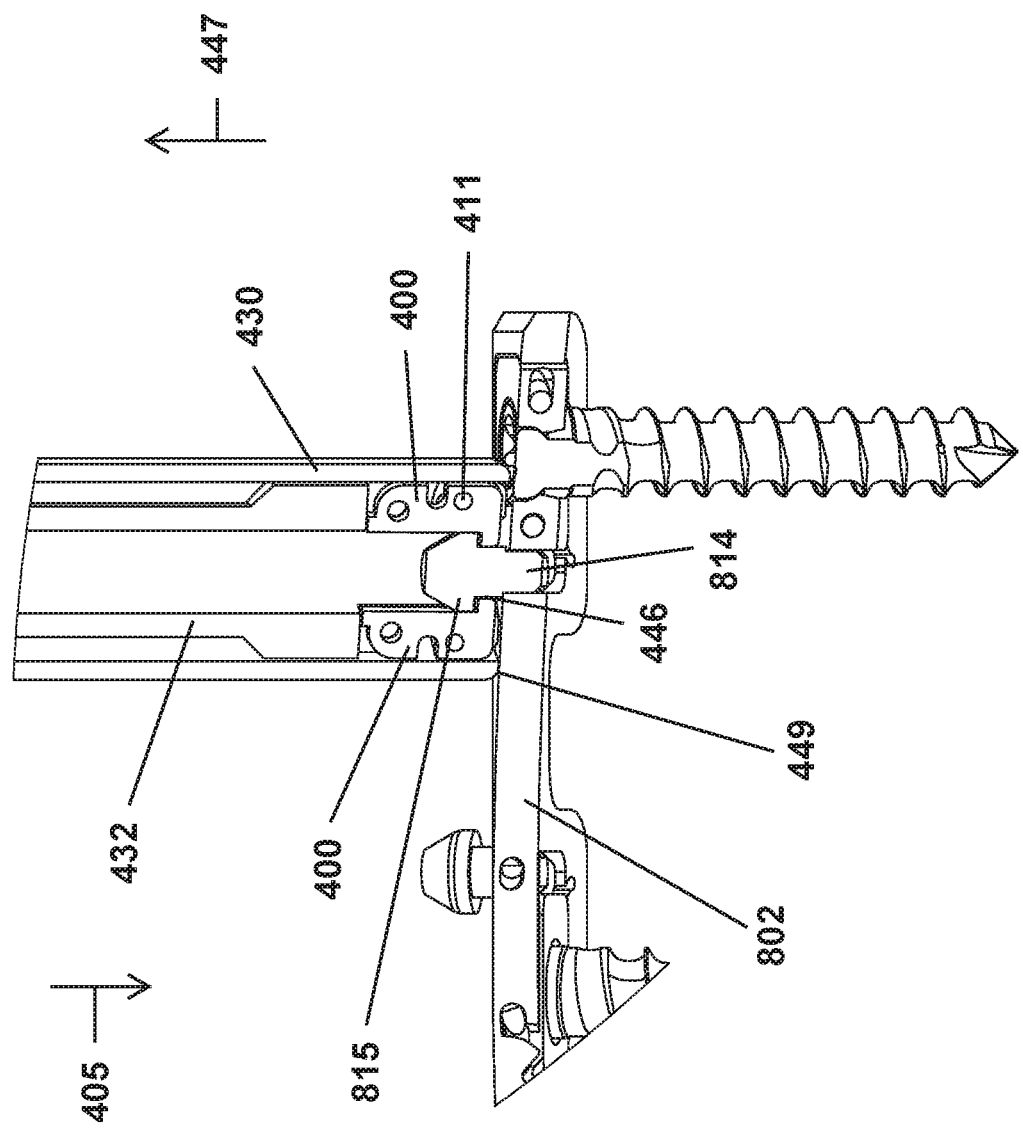
FIG. 21A is a cross-sectional view taken generally along line 21A-21A in FIG. 20 showing resilient fingers of the inner shaft engaging an underside of a head of a spacer of a bone plate system.
Figure 21B:
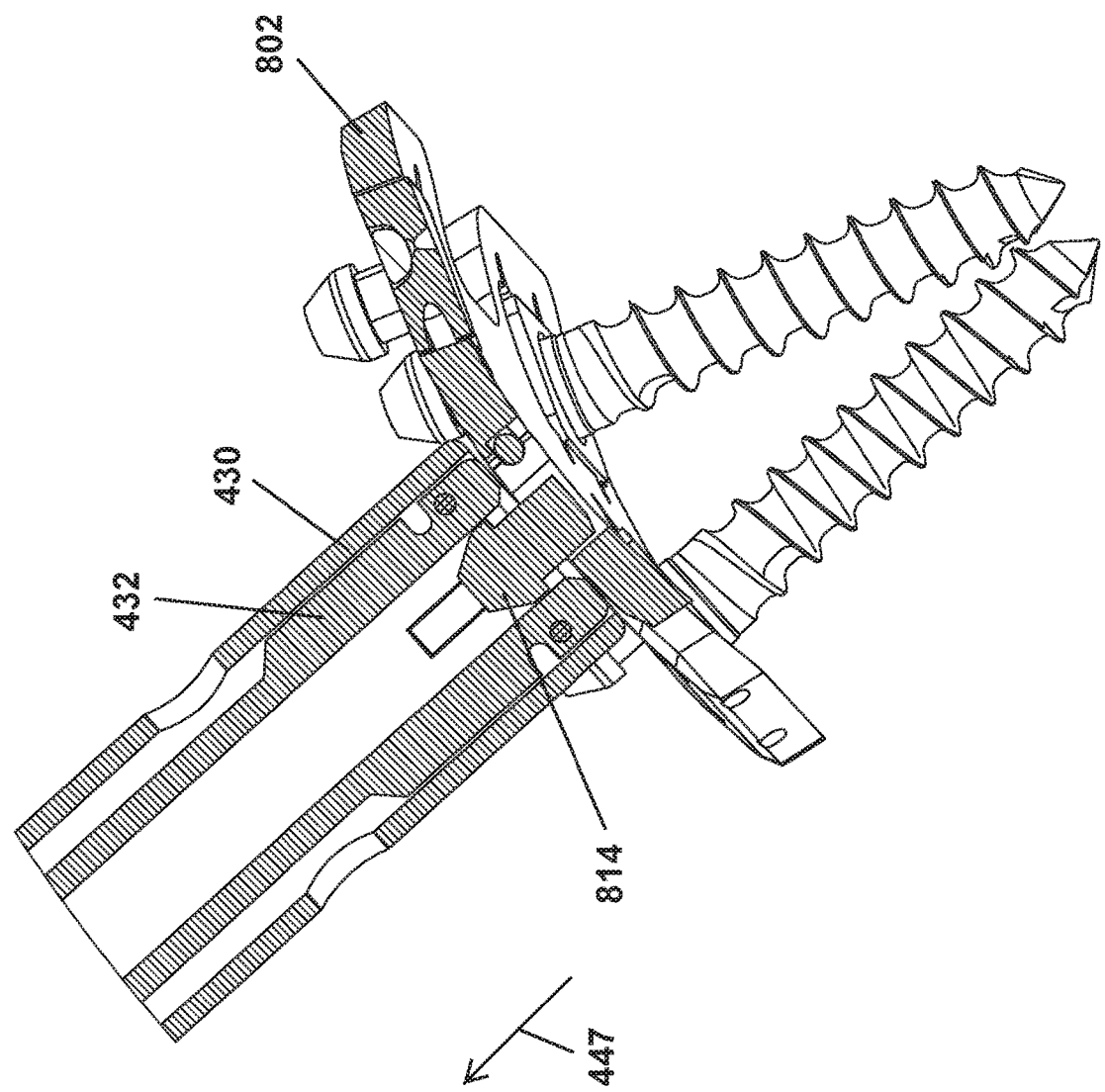
FIG. 21B is a cross-sectional view of the instrument and bone plate system of FIG. 21A taken generally perpendicular to the cross-section of FIG. 21A and showing the inner shaft engaged with the head of the spacer and the outer sleeve abutting an upper surface of the bone plate.
Figure 21C:
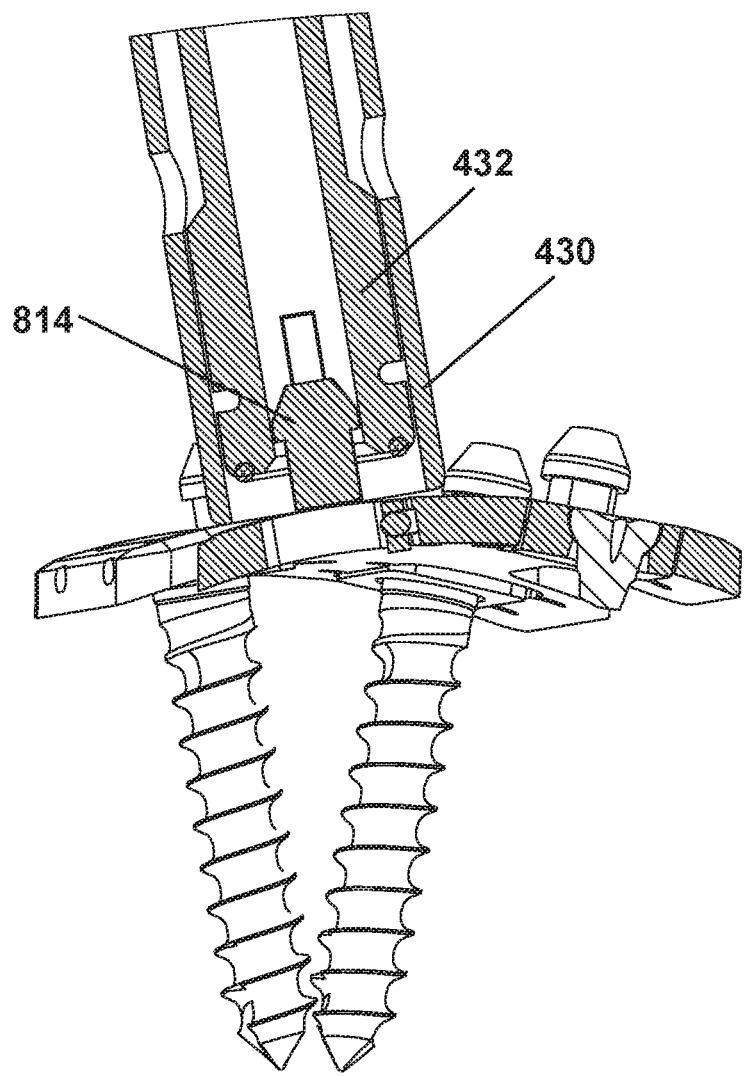
FIG. 21C is a cross-sectional view similar to FIG. 21B showing the inner shaft shifted proximally relative to the outer sleeve which removes the spacer from a gap between a slider and a wall of the bone plate.

With reference to FIGS. 21A-21C, a method is provided for removing a spacer 814 from a bone plate 802 of a bone plate system 800 (see FIG. 31) using the instrument 50. First, a user holds the instrument 50 so that the opening 446 of the inner shaft 432 is adjacent a head 815 of the spacer 814. The user advances the instrument 50 in direction 405 toward the bone plate 802 until the head 815 enters the opening 446 and the resilient fingers 400 snap below the head 815 of the spacer 814. The user then pivots the grip 426 in direction 450 (see FIG. 20) while pressing the instrument 50 against the bone plate 802. The pivoting of the grip 426 causes the inner shaft 432 to shift in direction 447 relative to the outer sleeve 430 and engages the resilient fingers 400 with the underside of the head 815. As the inner shaft 432 shifts in direction 447, a rim 449 of the outer sleeve 430 contacts the bone plate 802 and one of the sliders 808 therein. As shown in FIGS. 21B and 21C, the user's moving of the handle 426 toward the stationary grip 428 causes the inner shaft 432 to pull the spacer 814 in direction 447 outward from the bone plate 802.

Figure 21D:
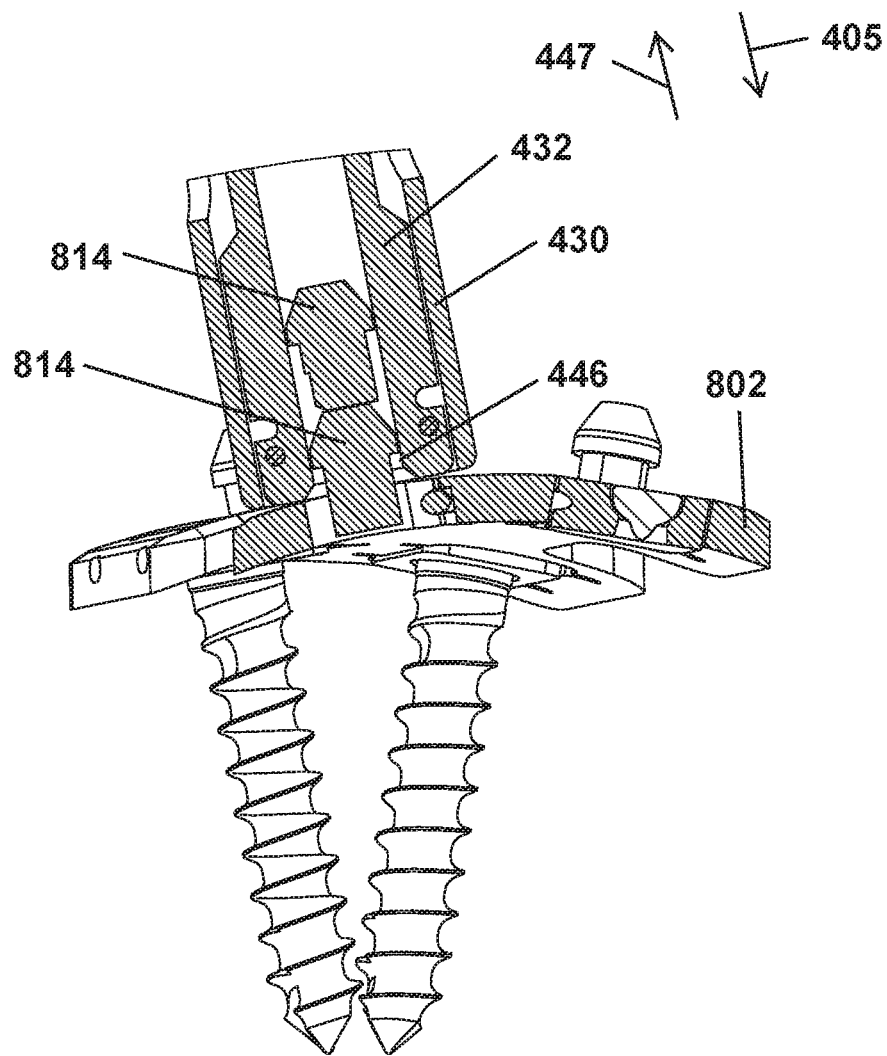
FIG. 21D is a cross-sectional view similar to FIG. 21B showing the inner shaft engaged with the head of a second spacer while the inner shaft contains a first spacer from a previous spacer-removing procedure.
Figure 21E:
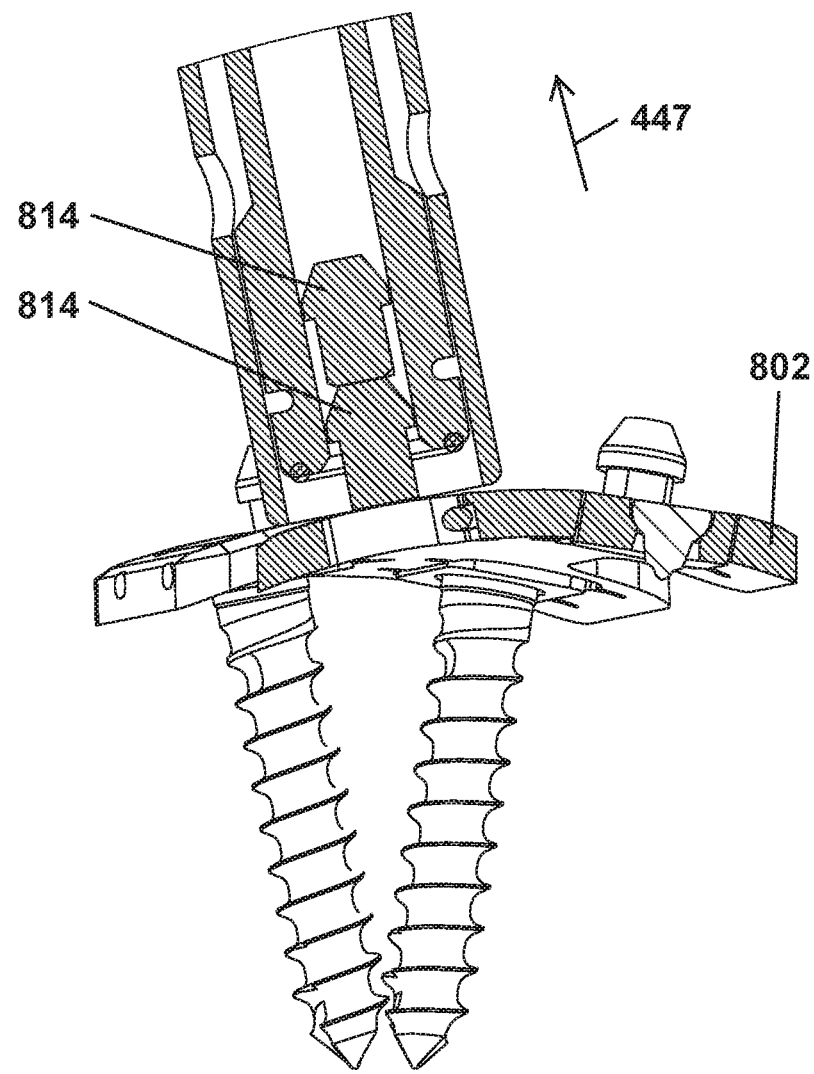
FIG. 21E is a cross-sectional view similar to FIG. 21D showing the inner shaft shifted proximally relative to the outer sleeve which removes the second spacer from a gap between a slider and a wall of the bone plate.

Once the spacer 814 has been removed from the bone plate 802, the user releases the handle 426 and the handle 426 may be biased back toward its initial position by a spring of the instrument 50. With reference to FIG. 21D, the user then positions the instrument 50 at a second spacer 814. Although the first spacer 814 is held by the resilient fingers 400 within the cannula 442, the user may simply press the instrument 50 in direction 405 onto the second spacer 814 which causes the second spacer 814 to shift the first spacer 814 farther into the cannula 442 and beyond the resilient fingers 400 as shown in FIG. 21D. The instrument 50 is pressed in direction 405 until the resilient fingers 400 snap below the head 815 of the second spacer. Next, the user pivots the handle 426 toward the stationary grip 428 which causes the inner shaft 432 to shift in direction 447, the outer sleeve to engage the bone plate 802/slider 808, and the inner shaft 432/resilient fingers 400 to pull the second spacer 814 out of the bone plate 802 as shown in FIGS. 21D and 21E.

Figure 22:
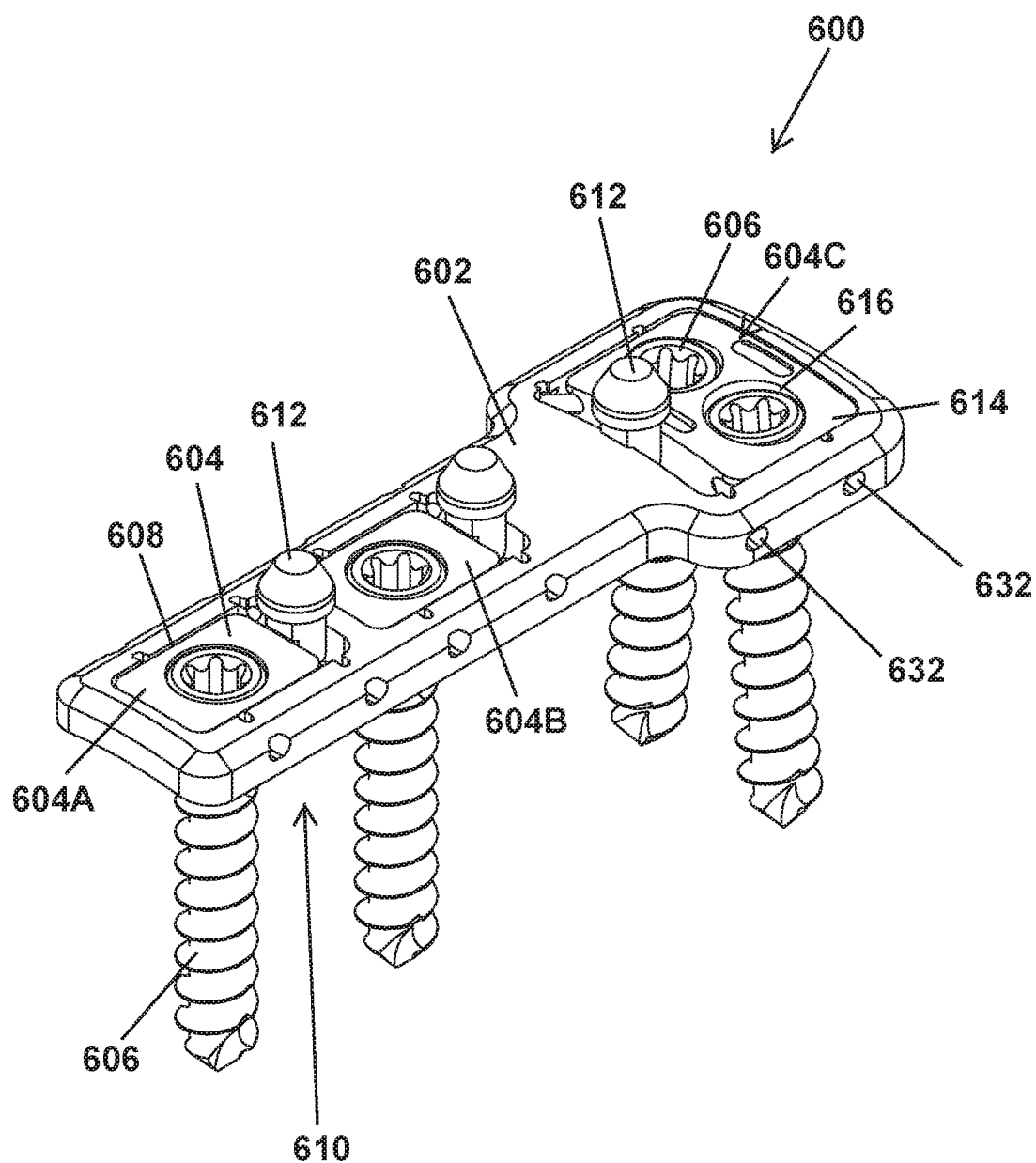
FIG. 22 is a perspective view of another bone plate system, the bone plate system having a slider assembly that receives two bones screws.

With reference to FIG. 22, a bone plate system 600 is provided that includes a bone plate 602 and slider assemblies 604 that receive bone screws 606 and are shifted along throughbores 608 of the bone plate 602 by biasing assemblies 610 once spacers 612 of the bone plate system 600 have been removed. The slider assemblies 604 include sliders 604A, 604B and 604C. The slider assemblies 604A, 604B are identical to the slider assemblies 16 discussed above. However, the slider assembly 604C is different and includes a slider 614 having two throughbores 616 for receiving two bone screws 606.

Figure 23:
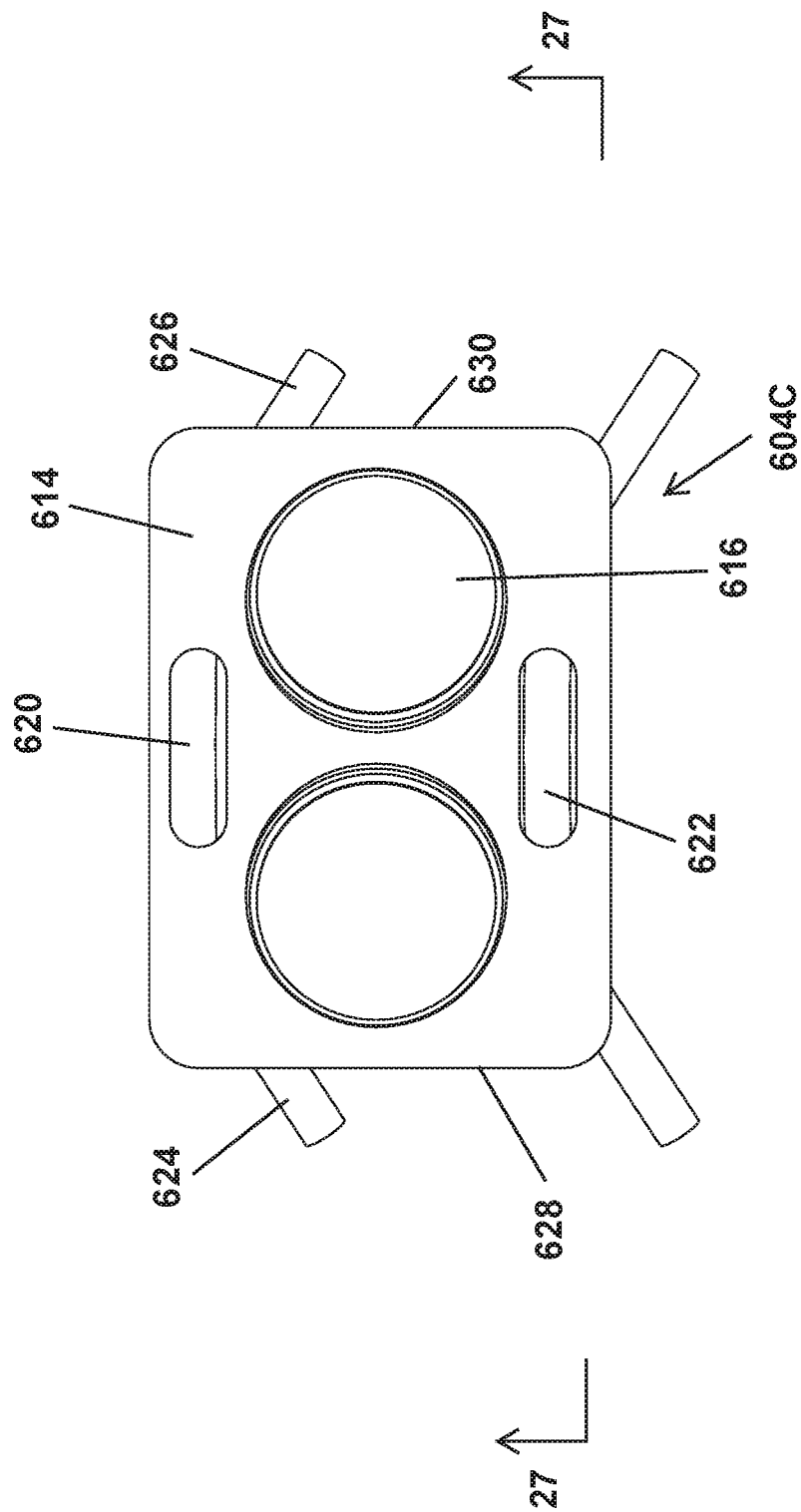
FIG. 23 is a top plan view of the two bone screw-receiving slider assembly of FIG. 22 including a slider and resilient wires having end portions that extend outward from sides of the slider.

With reference to FIG. 23, the slider assembly 604C includes the slider 614 and one or more resilient members, such as wires 620, 622. The wires 620, 622 each have end portions 624, 626 that extend outward from sides 628, 630 of the slider 614 and engage through apertures 632 of the bone plate 602.

Figure 24:
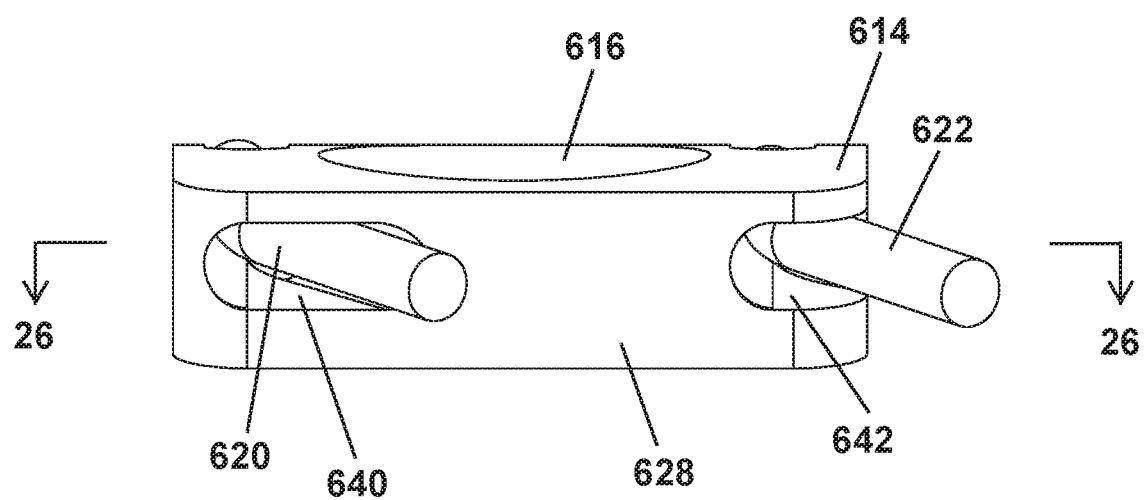
FIG. 24 is side elevational view of the slider assembly of FIG. 23 showing the end portions of the wires extending outward from passages of the slider.
Figure 25:
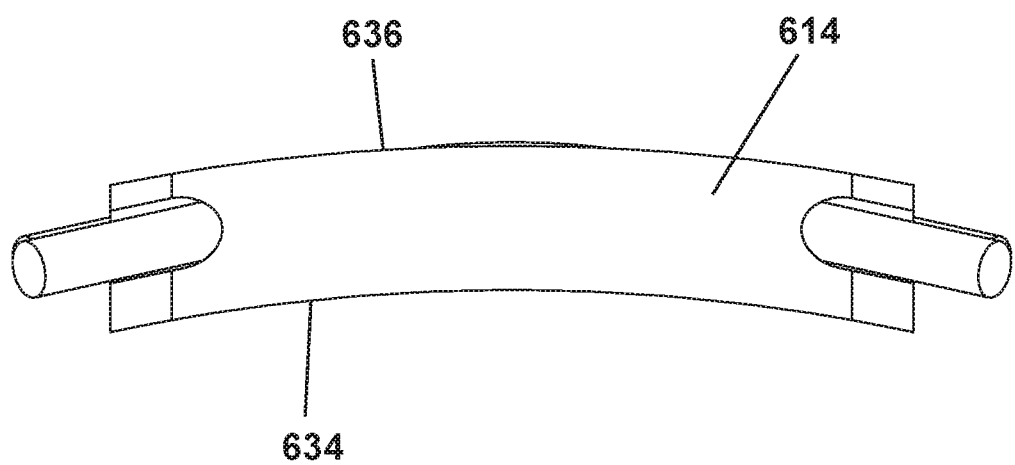
FIG. 25 is a front elevational view of the slider of FIG. 23 showing a curvature of the slider.

With reference to FIGS. 24 and 25, due to the lateral extent of the slider 614, the slider 614 has a curvature to compliment the curvature of an outer surface of a bone while minimizing interference with surrounding tissues. In the illustrated embodiment, the slider 614 includes a concave lower surface 634 and a convex upper surface 636. Due to the curvature of the slider 614, the wires 620, 622 have a complex curvature throughout the slider 614. More specifically and with reference to FIG. 24, the slider 614 includes passageways 640, 642 and the wires 620, 622 extend upwardly and to the left (as seen in FIG. 24) into the passageways 640, 642 at the side 628.

Figure 26:
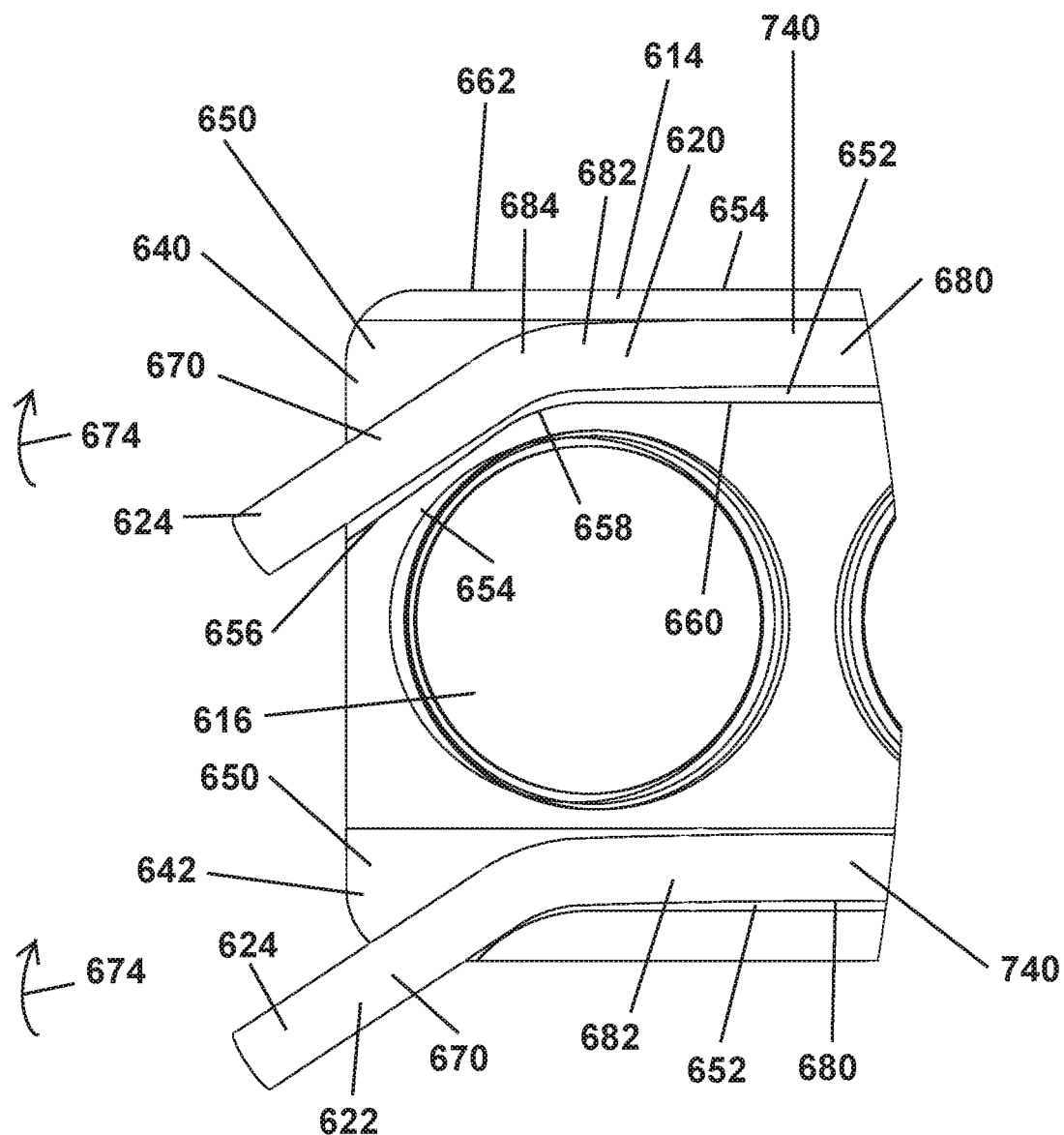
FIG. 26 is a cross-sectional view taken generally across line 26-26 in FIG. 24 showing the wires in loaded configuration and extending along an angled support surface and a curved support surface of the slider.

With reference to FIG. 26, the passageways 640, 642 each include an outer enlarged portion 650 and a narrow intermediate portion 652. The slider 614 includes a wall 654 extending around each throughbore 616 and the wall 654 includes an angled surface 656, curved corner 658, and an intermediate support surface 660. The slider 614 includes a wall 662 opposite the wall 654 and across the passageway 640. As discussed above with respect to the sliders 18, the outer enlarged portion 650 of the passageway 640, 642 permits movement of an outer intermediate portion 670 of the wires 620, 622 as the wires 620, 622 straighten from a loaded configuration to an unloaded configuration and the outer intermediate portions 670 pivot in direction 674. The wires 620, 622 include intermediate portions 680 that contain a bend 740 (see FIG. 29) out of the page in FIG. 26 as well as inner intermediate portions 682 that are connected to the outer intermediate portions 670 by bends 684 generally in the plane of the cross section taken of FIG. 26.

Figure 27:
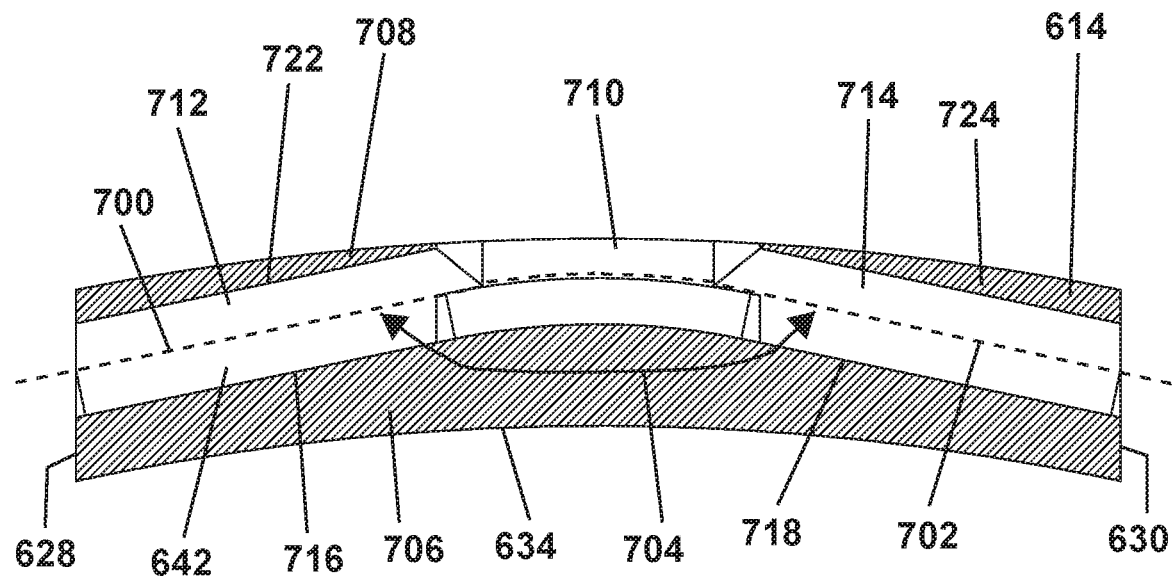
FIG. 27 is a cross-sectional view taken across line 27-27 in FIG. 23 showing an angle between portions of one of the passageways of the slider.

With reference to FIG. 27, the passageway 642 is shown and it will appreciated that the passageway 640 is similar in many respects. More specifically, the passageway 642 includes a first passageway portion 712 extending inward from side 628 and having an axis 700. The passageway 642 includes a second passageway portion 714 extending inward from the side 630 and having an axis 702 therein. There is an angle 704 between the axes 700, 702. The angle 704 forms a bend 740 (see FIG. 29) in the intermediate portion 680 of the wire 622 to provide enough material in a lower wall 706 of the slider 614 and accommodate the concave lower surface 634. The slider 614 includes an upper wall 708 having a through opening 710 therein that permits viewing of the wire 622. Through opening 710 may be formed during manufacture of the slider 614 by a machine tool that enters the passageway 642 from above and machines out material as needed. In other embodiments, the through opening 710 is not utilized such as if the slider 614 is produced using additive manufacturing. The lower wall 706 includes an inclined surface 716 in the first passage portion 712 to support one of the inner intermediate portions 682 of the wire 622 and an inclined surface 718 in the second passageway portion 714 to support the other inner intermediate portion 682. Likewise, the upper wall 708 includes inclined surfaces 722, 724 which together with the lower inclined surfaces 716, 718 maintain the bend 740 in the intermediate portion 680 whether the wire 622 is in the loaded or unloaded configuration thereof.

Figure 28:
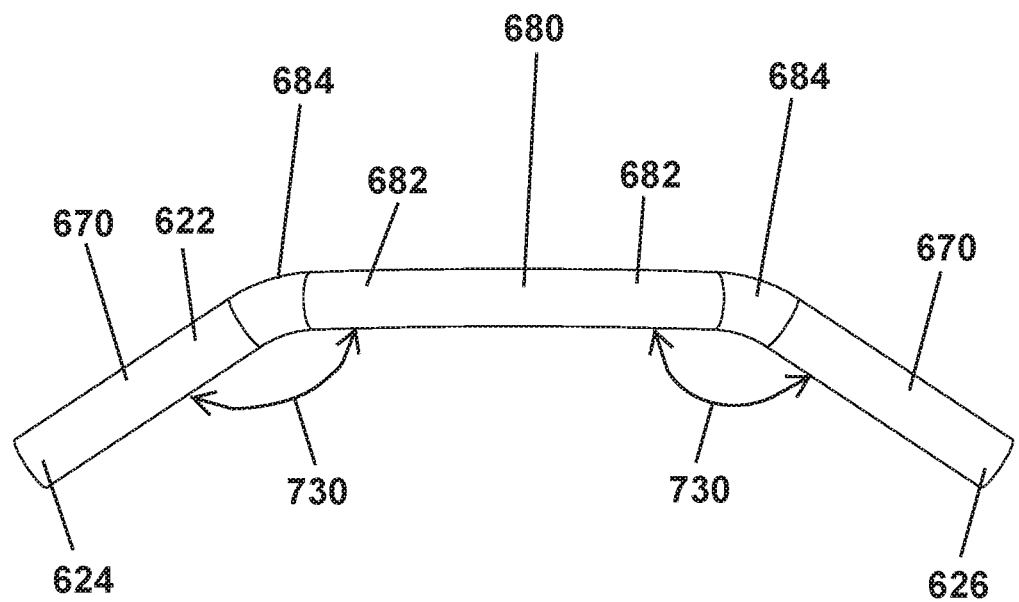
FIG. 28 is a top plan view of the resilient wire which extends through the passageway of FIG. 27 showing the wire in a loaded configuration.
Figure 29:
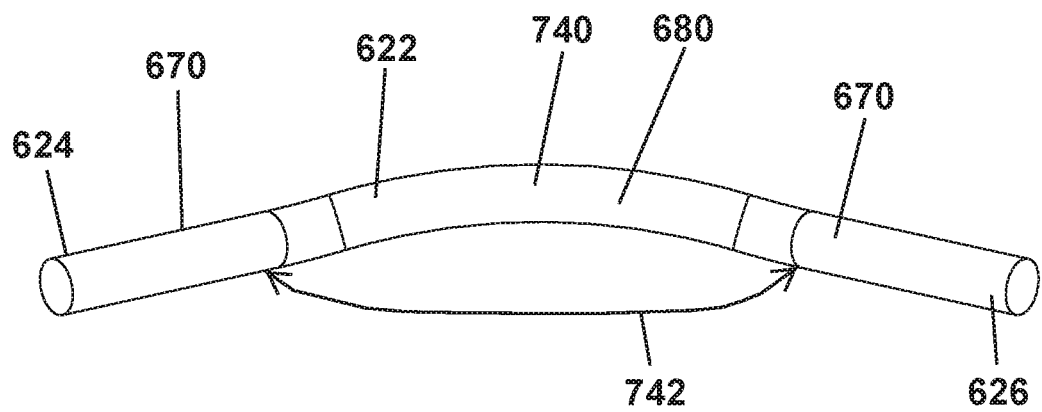
FIG. 29 is a front elevational view of the wire of FIG. 28 showing the wire in the loaded configuration.

With reference to FIG. 28, the wire 622 is shown removed from the slider 614 and is in the loaded configuration thereof. In the loaded configuration, the outer intermediate portion 670 is at an angle 730 relative to the inner intermediate portion 682 and forms two bends 684 in the wire 622. Whereas FIG. 28 is a top plan view, FIG. 29 is a rear elevation view of the wire 622 in the loaded configuration thereof. As discussed above with respect to FIG. 27, the first passageway portion 712 and the second passageway portion 714 create the bend 740 in the intermediate portion 680 of the wire 622 to provide clearance for the concave lower surface 634 of the slider 714. The bend 740 positions the outer intermediate portions 670 at an angle 742 relative to one another. Thus, when the wires 620, 622 are in the loaded configuration, each wire 620, 622 has three bends including the two bends 684 and the bend 740. Once the spacer 612 has been removed from the bone plate 602 and the pins 620, 622 urge the slider 614 to an unloaded position thereof, the bends 684 straighten out in a manner similar to the straightening of the bend 295 as one goes from FIG. 15 to FIG. 16. However, even once the slider 614 has shifted to the unloaded position, the passageways 640, 642 maintain the bend 740 in the intermediate portions 680 of the wires 620, 622 because the inner intermediate portions 682 are constrained against movement unlike the outer intermediate portions 670.

Figure 30:
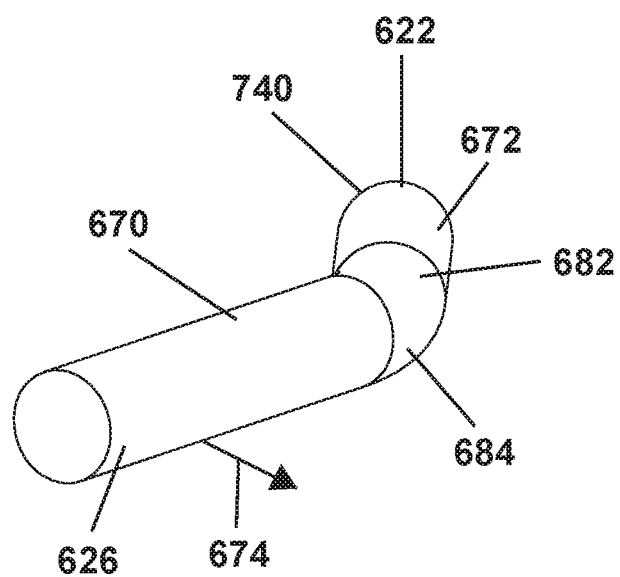
FIG. 30 is a side elevational view of the wire of FIG. 28 in the loaded configuration.

With reference to FIG. 30, the wire 622 is shown in a side elevational view to illustrate how each of the bends 684 orients the outer intermediate portion 670 thereof to extend transversely to the inner intermediate portions 682. Further, the bend 740 provides the vertical component (as shown in FIG. 30) of the extent of both the outer intermediate portion 670 and the inner intermediate portion 672 of the wire 622. When the spacers 612 are removed from the bone plate 602, the outer intermediate portions 670 pivot in direction 674.

Figure 31:
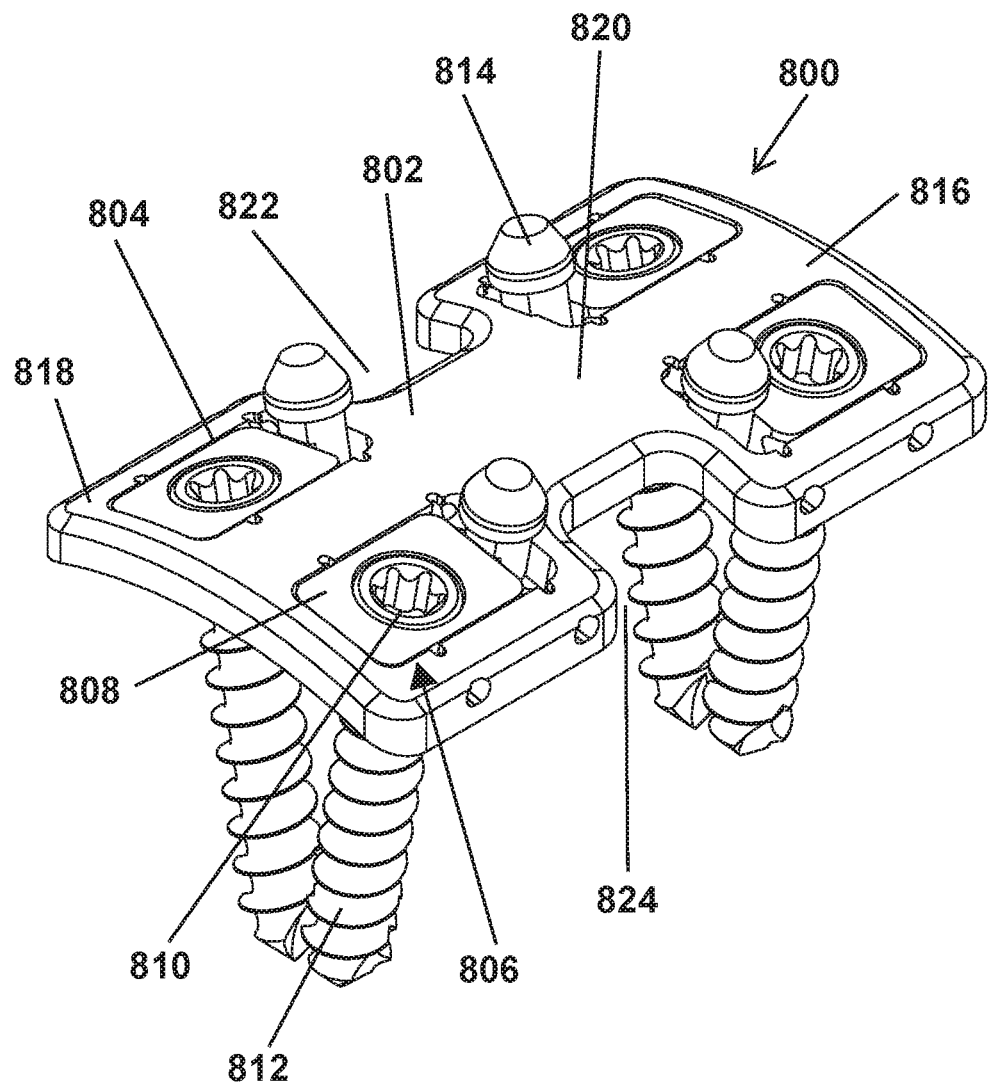
FIG. 31 is a perspective view of a bone plate system having a dog bone-shaped bone plate.
Figure 32:
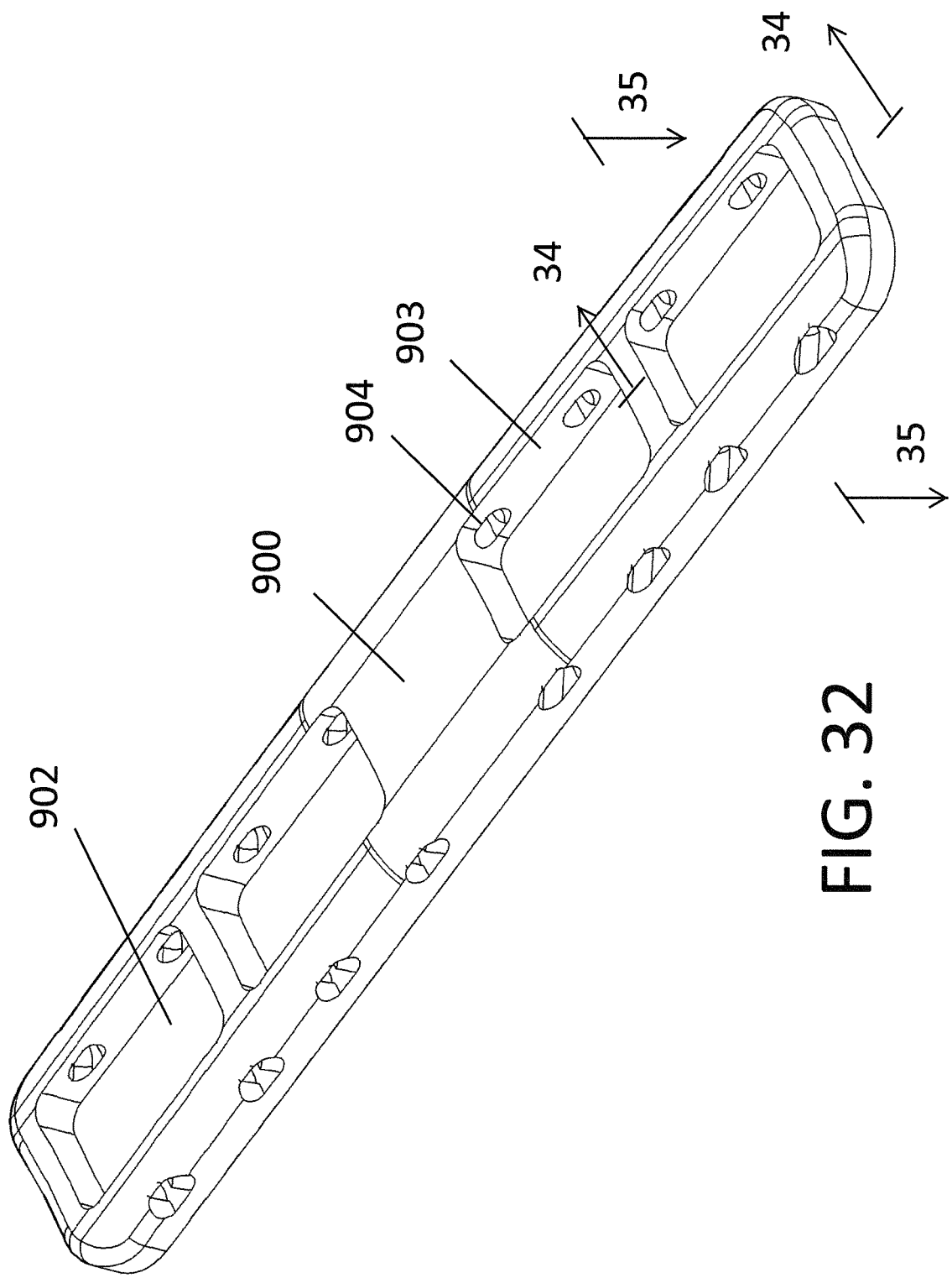
FIG. 32 is a perspective view of another bone plate having through openings for receiving sliders and openings in side walls of the bone plate for receiving resilient wires that urge the sliders in predetermined directions within the throughbores.
Figure 33:
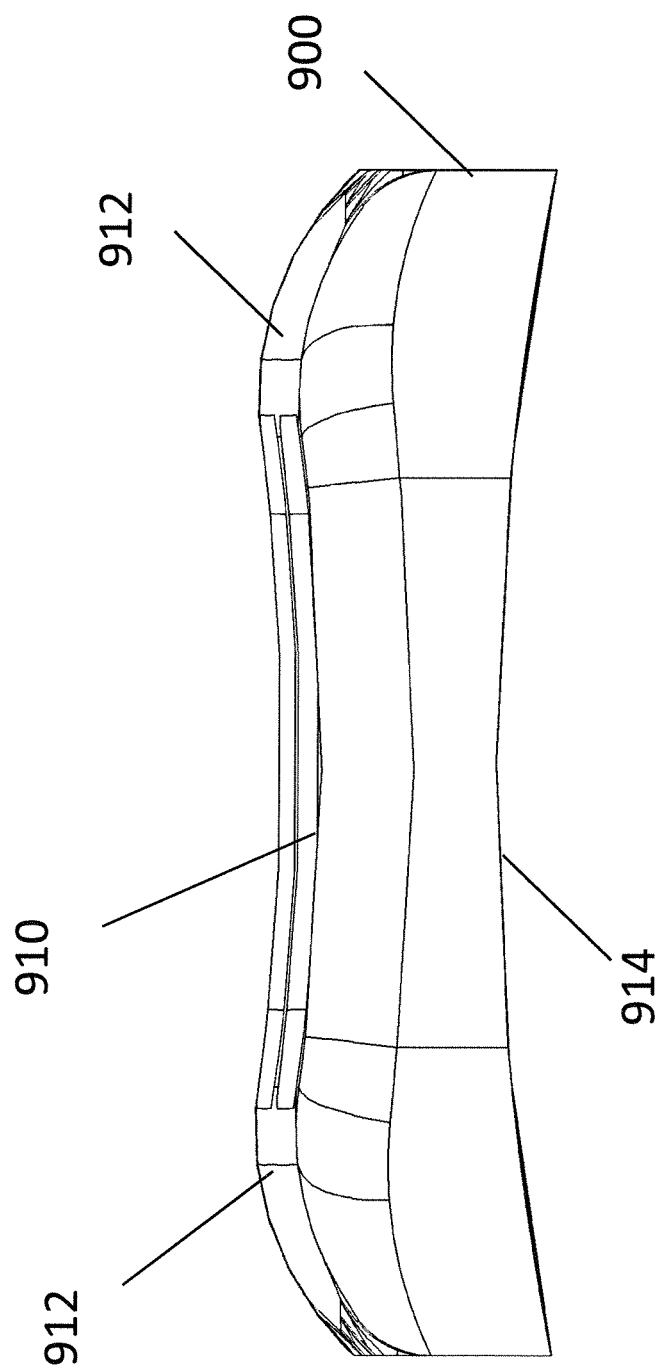
FIG. 33 is an end elevational view of the bone plate of FIG. 32 showing a reduced thickness of the bone plate in a middle of the bone plate.
Figure 34:
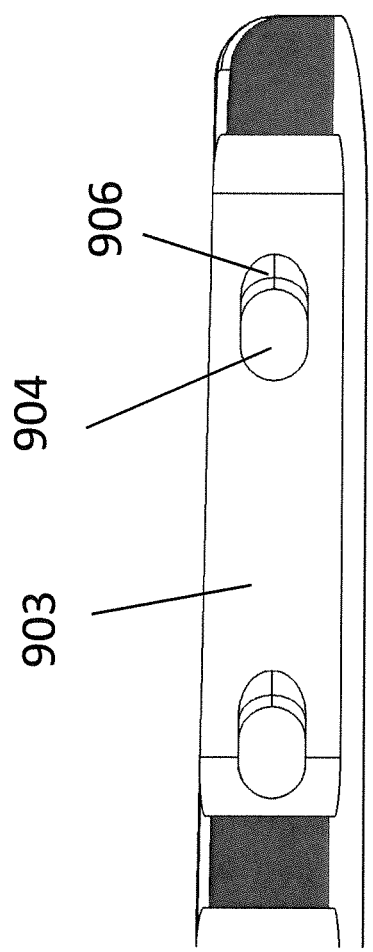
FIG. 34 is a cross-sectional view of a portion of the bone plate of FIG. 32 taken across line 34-34 in FIG. 32 showing apertures in one of the side walls of the bone plate for receiving the resilient wires of a slider received in the associated through opening.
Figure 35:
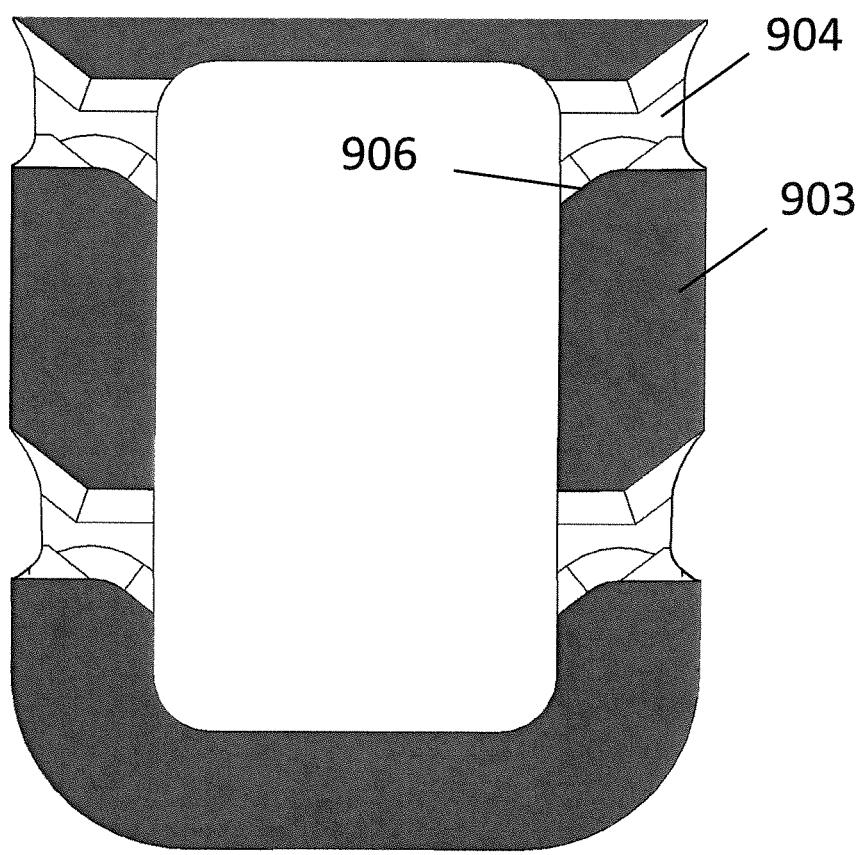
FIG. 35 is a cross-sectional view of a portion of the bone plate of FIG. 32 taken across line 35-35 in FIG. 32 showing the geometry of the apertures of the side walls of the bone plate.

With reference to FIG. 31, the bone plate system 800 is similar in many respects to the bone plate system 10 discussed above. The bone plate system 800 includes a bone plate 802 having through openings 804 that receive slider assemblies 806. The slider assemblies 806 include sliders 808 having throughbores 810 that receive bone screws 812. The bone plate system 800 includes spacers 814 that may be removed from the bone plate 802 to permit the slider assemblies 806 to shift to unloaded positions which compresses bones connected to the bone screws 812. One difference between the bone plate system 800 and the bone plate system 10 discussed above is that the bone plate 802 has a dog bone-shaped configuration with enlarged end portions 816, 818 and a narrowed intermediate portion 820. The narrowed intermediate portion 820 forms notches 822, 824 on opposite sides of the bone plate 802. Each end portion 816, 818 includes two throughbores 810 to receive two slider assemblies 806.

Regarding FIGS. 32-35, a bone plate 900 is provided that is similar in many respects to the bone plate 12 discussed above. The bone plate 900 may be utilized in the bone plate system 10 instead of the bone plate 12. For example, the bone plate 900 includes through openings 902 configured to receive the slider assemblies 16. The bone plate 900 includes side walls 903 with apertures 904 for receiving end portions of the wires 20, 22 of the slider assemblies 16. Regarding FIGS. 34 and 35, each aperture 904 includes an angled surface 906 for supporting the associated wire 20, 22 and providing a more gradual bend of the wire 20, 22 when the sliders 18 are held in the loaded configuration in the through openings 902 by the spacers 36. Regarding FIG. 33, the bone plate 12 has a varying thickness between upper and lower surfaces thereof including a thinner intermediate portion 910 between thicker side portions 912. The thinner intermediate portion 910 may include, for example, a generally concave surface portion. Conversely, the lower surface 914 of the bone plate 900 may have a generally concave surface portion. The thinner intermediate portion 910 provides a reduced thickness along the midline of the plate which may improve interaction with surrounding tissues for some patients.

While there have been illustrated and described particular embodiments of the present invention, it will be appreciated that numerous changes and modifications will occur to those skilled in the art, and it is intended for the present invention to cover all those changes and modifications which fall within the scope of the appended claims.

What is claimed is:

1. A bone plate system comprising:
   a bone plate;
   a plurality of elongated through openings of the bone plate, each elongated through opening having a pair of end portions across the through opening from each other;
   a plurality of bone screws each having a head portion and a shank portion, the shank portion configured to be driven into bone;
   a plurality of sliders in the elongated through openings and having throughbores configured to receive the head portions of the bone screws, the sliders and the bone screw head portions received therein being shiftable within the elongated through openings relative to the bone plate;
   at least one resilient member having a loaded configuration wherein the at least one resilient member is configured to apply a biasing force to the sliders and urge each of the sliders toward one end portion of a respective through opening;
   at least one actuator having an interference position in which the actuator maintains the at least one resilient member in the loaded configuration and inhibits shifting of the sliders toward the one end portion of the respective through openings and a clearance position in which the actuator permits the at least one resilient member to urge the sliders and the bone screws received therein along the through openings of the rigid bone plate and toward the one end portion of the through openings; and
   wherein the at least one resilient member in the loaded configuration thereof contacts the bone plate and the sliders and applies the biasing force to the sliders to urge the sliders toward the one end portion of the through openings.

2. The bone plate system of claim 1 wherein the at least one actuator in the interference position thereof keeps each of the sliders at an opposite end portion of the respective through opening.

3. The bone plate system of claim 1 wherein the at least one resilient member includes a plurality of elongated resilient wires each associated with one of the sliders.

4. The bone plate system of claim 1 wherein the at least one resilient member includes a pair of resilient members secured to each of the sliders, each resilient member having a pair of portions connecting the slider to the bone plate.

5. The bone plate system of claim 1 wherein the at least one actuator includes a plurality of actuators each having a head portion configured to be engaged by an actuator removal instrument and a body portion held between one of the sliders and the bone plate with the actuator in the interference position.

6. The bone plate system of claim 1 wherein the bone plate includes a flat wall portion extending along one of the through openings and one of the sliders includes a flat wall portion facing the flat wall portion of the bone plate; and the at least one actuator has a pair of flats engaged with the flat wall portions of the bone plate and the one slider with the actuator in the interference position.

7. The bone plate system of claim 1 wherein at least one of the sliders includes a pair of through bores sized to receive head portions of a pair of bone screws.

8. The bone plate system of claim 1 wherein the bone plate has a unitary, one-piece construction.

9. The bone plate system of claim 1 wherein the sliders are rigid and do not deform with seating of the bone anchor head portions in the throughbores of the sliders.

10. The bone plate system of claim 1 wherein the at least one resilient member is in the loaded configuration with the at least one actuator in the interference position and applies a biasing force against each of the sliders to clamp the at least one actuator between the sliders and the bone plate, and the at least one resilient member shifts toward an unloaded configuration with the at least one actuator in the clearance position.

11. The bone plate system of claim 1 wherein there is a single slider in each of the elongated through openings of the bone plate.

12. The bone plate system of claim 1 wherein the bone plate and the slider have openings and surfaces defining the openings;
   wherein the at least one resilient member extends in the openings; and
   wherein the at least one resilient member engages the surfaces defining the openings of the bone plate and slider with the actuator in the interference position.

13. A bone plate system comprising:
   a bone plate;
   a plurality of elongated through openings of the bone plate, each elongated through opening having a pair of end portions across the through opening from each other;
   a plurality of bone screws each having a head portion and a shank portion, the shank portion configured to be driven into bone;
   a plurality of sliders in the elongated through openings and having throughbores configured to receive the head portions of the bone screws, the sliders and the bone screw head portions received therein being shiftable within the elongated through openings relative to the bone plate;
   at least one resilient member for being configured to apply a biasing force to the sliders to urge each of the sliders toward one end portion of a respective through opening;
   at least one actuator having an interference position in which the actuator inhibits shifting of the sliders toward the one end portion of the respective through openings and a clearance position in which the actuator permits the at least one resilient member to urge the sliders and the bone screws received therein along the through openings of the rigid bone plate and toward the one end portion of the through openings; and
   wherein the at least one resilient member includes a plurality of elongated resilient members each having a pair of opposite end portions and an intermediate portion between the end portions, the intermediate portion supported by one of the sliders and the end portions supported by the bone plate.

14. A bone plate system comprising:
   a bone plate;

a plurality of elongated through openings of the bone plate, each elongated through opening having a pair of end portions across the through opening from each other;

a plurality of bone screws each having a head portion and a shank portion, the shank portion configured to be driven into bone;

a plurality of sliders in the elongated through openings and having throughbores configured to receive the head portions of the bone screws, the sliders and the bone screw head portions received therein being shiftable within the elongated through openings relative to the bone plate;

at least one resilient member for being configured to apply a biasing force to the sliders to urge each of the sliders toward one end portion of a respective through opening;

at least one actuator having an interference position in which the actuator inhibits shifting of the sliders toward the one end portion of the respective through openings and a clearance position in which the actuator permits the at least one resilient member to urge the sliders and the bone screws received therein along the through openings of the rigid bone plate and toward the one end portion of the through openings; and wherein the at least one resilient member includes a plurality of resilient members each extending between one of the sliders and the bone plate, each resilient member having a deformed configuration including a bent portion with the at least one actuator in the interference position, the bent portion being allowed to straighten toward a non-deformed configuration thereof with the at least one actuator in the clearance position.

15. A bone plate system for securing a pair of bones, the bone plate system comprising:

a bone plate;

a pair of elongated through openings of the bone plate;

a pair of bone screws for securing the bone plate to the pair of bones, each bone screw having a head portion and a shank portion;

a pair of sliders in the elongated through openings of the bone plate, each slider having a through bore configured to permit the shank portion of one of the bone screws to be driven through the through bore and into a bone and the head portion to be seated in the through bore;

at least one actuator configured to be clamped between the sliders and the bone plate;

at least one resilient member extending in the through openings of the bone plate between the bone plate and the sliders, the at least one resilient member configured for applying a biasing force to the sliders to urge the sliders against the at least one actuator and cause the sliders to clamp the at least one actuator between the sliders and the bone plate; and the at least one actuator being removable from being clamped between the sliders and the bone plate so that the biasing force applied by the at least one resilient member extending in the through openings of the bone plate urges each slider and the bone screw therein toward the other slider and bone screw for compressing the bones together.

16. The bone plate system of claim 15 wherein the at least one resilient member includes at least one elongated resilient wire.

17. The bone plate system of claim 15 wherein the at least one resilient member includes at least one resilient member associated with each of the sliders.

18. The bone plate system of claim 17 wherein the at least one resilient member connects the associated slider to the bone plate and supports the slider in the through opening of the bone plate.

19. The bone plate system of claim 17 wherein each slider includes a pair of support surfaces extending transversely to one another and the at least one resilient member associated with the slider has a loaded configuration wherein portions of the resilient member extend along the support surfaces and an unloaded configuration wherein the portions of the resilient member are spaced from the support surfaces.

20. The bone plate system of claim 15 wherein each slider includes opposite sides and at least one passageway extending intermediate the sides sized to permit the at least one resilient member to extend therethrough.

21. The bone plate system of claim 15 wherein the at least one actuator includes a plurality of actuators each having a head portion configured to be engaged by an actuator removal instrument and a body portion for being clamped between one of the sliders and the bone plate and resisting shifting of the slider toward the other slider.

22. The bone plate system of claim 15 wherein the at least one resilient member includes superelastic nitinol.

23. The bone plate system of claim 15 wherein the at least one resilient member including an elongate resilient member having a first portion secured to the bone plate, a second portion secured to one of the sliders, and an intermediate portion between the first and second portions along the elongate resilient member extending from the bone plate to the one slider.

24. The bone plate system of claim 15 wherein the bone plate includes a first opening and the slider includes a second opening; and wherein the at least one resilient member extends in the first and second openings.

25. A bone plate system for securing a pair of bones, the bone plate system comprising:

a bone plate;

a pair of elongated through openings of the bone plate;

a pair of bone screws for securing the bone plate to the pair of bones, each bone screw having a head portion and a shank portion;

a pair of sliders in the elongated through openings of the bone plate, each slider having a through bore configured to permit the shank portion of one of the bone screws to be driven through the through bore and into a bone and the head portion to be seated in the through bore;

at least one actuator configured to be clamped between the sliders and the bone plate;

at least one resilient member configured for applying a biasing force to the sliders to urge the sliders against the at least one actuator and cause the sliders to clamp the at least one actuator between the sliders and the bone plate; and the at least one actuator being removable from being clamped between the sliders and the bone plate so that the biasing force urges each slider and the bone screw therein toward the other slider and bone screw for compressing the bones together; and wherein the at least one resilient member includes at least one elongated resilient wire;

wherein the at least one elongated resilient wire includes a pair of elongated resilient wires secured to each of the sliders that connect the sliders to the bone plate.

26. A bone plate system for securing a pair of bones, the bone plate system comprising:
a bone plate;
a pair of elongated through openings of the bone plate;
a pair of bone screws for securing the bone plate to the pair of bones, each bone screw having a head portion and a shank portion;
a pair of sliders in the elongated through openings of the bone plate, each slider having a through bore configured to permit the shank portion of one of the bone screws to be driven through the through bore and into a bone and the head portion to be seated in the through bore;
at least one actuator configured to be clamped between the sliders and the bone plate;
at least one resilient member configured for applying a biasing force to the sliders to urge the sliders against the at least one actuator and cause the sliders to clamp the at least one actuator between the sliders and the bone plate;
the at least one actuator being removable from being clamped between the sliders and the bone plate so that the biasing force urges each slider and the bone screw therein toward the other slider and bone screw for compressing the bones together; and
wherein the at least one resilient member includes at least one bend with the actuator clamped between the sliders and the bone plate and the at least one bend straightens in response to the at least one actuator being removed from being clamped between the sliders and the bone plate.

27. A bone plate system for securing a pair of bones, the bone plate system comprising:
a bone plate;
a pair of elongated through openings of the bone plate;
a pair of bone screws for securing the bone plate to the pair of bones, each bone screw having a head portion and a shank portion;
a pair of sliders in the elongated through openings of the bone plate, each slider having a through bore configured to permit the shank portion of one of the bone screws to be driven through the through bore and into a bone and the head portion to be seated in the through bore;
at least one actuator configured to be clamped between the sliders and the bone plate;
at least one resilient member configured for applying a biasing force to the sliders to urge the sliders against the at least one actuator and cause the sliders to clamp the at least one actuator between the sliders and the bone plate; and
the at least one actuator being removable from being clamped between the sliders and the bone plate so that the biasing force urges each slider and the bone screw therein toward the other slider and bone screw for compressing the bones together;
wherein each slider includes opposite sides and at least one passageway extending intermediate the sides sized to permit the at least one resilient member to extend therethrough; and
wherein the at least one resilient member has a pair of portions that pivot within the passageway in response to the at least one actuator being removed from being clamped between the sliders and the bone plate and the at least one passageway includes an enlarged portion at each of the sides that permits the pivotal movement of the portions of the resilient member.

28. A bone plate system for securing a pair of bones, the bone plate system comprising:
a bone plate;
a pair of elongated through openings of the bone plate;
a pair of bone screws for securing the bone plate to the pair of bones, each bone screw having a head portion and a shank portion;
a pair of sliders in the elongated through openings of the bone plate, each slider having a through bore configured to permit the shank portion of one of the bone screws to be driven through the through bore and into a bone and the head portion to be seated in the through bore;
at least one actuator configured to be clamped between the sliders and the bone plate;
at least one resilient member configured for applying a biasing force to the sliders to urge the sliders against the at least one actuator and cause the sliders to clamp the at least one actuator between the sliders and the bone plate;
the at least one actuator being removable from being clamped between the sliders and the bone plate so that the biasing force urges each slider and the bone screw therein toward the other slider and bone screw for compressing the bones together;
wherein each slider includes opposite sides and at least one passageway extending intermediate the sides sized to permit the at least one resilient member to extend therethrough; and
wherein the at least one passageway includes a pair of passageways extending intermediate the sides and the at least one resilient member includes a pair of resilient wires associated with each of the sliders that extend through the passageways.

* * * * *